United States Patent
Rhodes et al.

(10) Patent No.: US 8,163,027 B2
(45) Date of Patent: Apr. 24, 2012

(54) TIBIAL INSERT HAVING A REINFORCED KEEL

(75) Inventors: James Matthew Rhodes, Warsaw, IN (US); Jordan Soonja Lee, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 219 days.

(21) Appl. No.: 11/425,929

(22) Filed: Jun. 22, 2006

(65) Prior Publication Data
US 2007/0299530 A1 Dec. 27, 2007

(51) Int. Cl.
*A61F 2/38* (2006.01)
(52) U.S. Cl. .................. 623/20.34; 623/20.32
(58) Field of Classification Search .............. 623/20.32, 623/20.34, 23.14, 23.19, 23.2, 23.21, 23.62, 623/23.63
See application file for complete search history.

(56) References Cited

U.S. PATENT DOCUMENTS

| | | | |
|---|---|---|---|
| D245,259 S | 8/1977 | Shen | |
| 4,895,572 A | 1/1990 | Chernoff | |
| 4,919,671 A | 4/1990 | Karpf | |
| 4,978,357 A | 12/1990 | Goymann et al. | |
| 5,152,797 A | 10/1992 | Luckman et al. | |
| 5,171,276 A | 12/1992 | Caspari et al. | |
| 5,336,266 A | 8/1994 | Caspari et al. | |
| 5,383,937 A | 1/1995 | Mikhail | |
| 5,458,653 A * | 10/1995 | Davidson | 623/23.36 |
| 5,509,934 A | 4/1996 | Cohen | |
| 5,549,683 A | 8/1996 | Bonutti | |
| 6,102,954 A * | 8/2000 | Albrektsson et al. | 623/20.32 |
| 6,139,580 A | 10/2000 | Wurzinger et al. | |
| 6,217,617 B1 | 4/2001 | Bonutti | |
| 6,267,785 B1 | 7/2001 | Masini | |
| 6,364,910 B1 | 4/2002 | Shultz et al. | |
| 6,699,289 B2 | 3/2004 | Lannotti et al. | |
| 6,939,135 B2 * | 9/2005 | Sapian | 433/174 |
| 7,179,295 B2 | 2/2007 | Kovacevic | |
| 7,294,149 B2 | 11/2007 | Hozack | |
| 7,615,054 B1 | 11/2009 | Bonutti | |
| 2001/0037153 A1 | 11/2001 | Rockwood, Jr. et al. | |
| 2003/0060884 A1 | 3/2003 | Fell | |
| 2003/0125809 A1 * | 7/2003 | Iannotti et al. | 623/19.13 |
| 2004/0006393 A1 * | 1/2004 | Burkinshaw | 623/20.3 |
| 2004/0083005 A1 | 4/2004 | Jacobsson et al. | |
| 2004/0113790 A1 | 6/2004 | Hamel et al. | |

(Continued)

FOREIGN PATENT DOCUMENTS

DE 8708501 U1 4/1988

(Continued)

OTHER PUBLICATIONS

European Search Report for European Patent Application No. 07252488.7-2310, Nov. 15, 2007, 8 pgs.

(Continued)

*Primary Examiner* — David Isabella
*Assistant Examiner* — Joshua Levine
(74) *Attorney, Agent, or Firm* — Barnes & Thornburg LLP

(57) ABSTRACT

A tibial insert includes a platform defining an upper bearing surface and a bottom surface. A keel of the tibial insert is coupled to the bottom surface of the platform and a rod of the tibial insert extends through a portion of the keel. A surgical method for knee arthroplasty is also disclosed.

11 Claims, 12 Drawing Sheets

U.S. PATENT DOCUMENTS

| | | | |
|---|---|---|---|
| 2005/0059972 A1* | 3/2005 | Biscup | 606/73 |
| 2005/0125068 A1 | 6/2005 | Hozack et al. | |
| 2005/0143731 A1 | 6/2005 | Justin et al. | |
| 2005/0165317 A1 | 7/2005 | Turner et al. | |
| 2007/0260322 A1 | 11/2007 | Nowakowski | |

FOREIGN PATENT DOCUMENTS

| | | |
|---|---|---|
| DE | 4219808 C1 | 12/1993 |
| DE | 102004053075 | 5/2006 |
| EP | 0290736 | 11/1988 |
| EP | 0552950 A1 | 7/1993 |
| EP | 0709073 A1 | 5/1996 |
| EP | 0925765 | 6/1999 |
| EP | 0925765 A2 | 6/1999 |
| EP | 1136045 A2 | 9/2001 |
| EP | 1738718 | 1/2007 |
| FR | 2698536 | 6/1994 |
| WO | 9322990 | 11/1993 |
| WO | 00/13585 A1 | 3/2000 |
| WO | 00/36998 A1 | 6/2000 |
| WO | 01/49173 A1 | 7/2001 |
| WO | 2005/120203 A2 | 12/2005 |

OTHER PUBLICATIONS

"The Comprehensive Natural-Knee Family", 2005 Zimmer, Inc., www.zimmer.com (4 pages).

"M/G Unicompartmental Knee System", 2005 Zimmer, Inc., www.zimmer.com (2 pages).

"Zimmer Unicompartmental High Flex Knee System—Built on Success", 2005 Zimmer, Inc. www.zimmer.com (3 pages).

"Preservation Uni-Compartmental Knee", Surgical Technique Booklet, 2002 DePuy Orthopaedics, Inc. 0612-04-500 (Rev, 2).

"Zimmer Travecular Metal Femoral Cone Augment Surgical Technique", Surgical Technique Booklet, 2005, Zimmer, Inc. (10 pages).

"Surgical Technique for Nexgen Primary Porous Patella* With Trabecular Metal", Surgical Technique Booklet, 2001, Zimmer, Inc. (16 pages).

"Surgical Technique for Nexgen Curciate Retaining [CR] and Legacy Knee Posterior Stabilized [LPS] Trabecular Metal Monoblock Tibias", Surgical Technique Booklet, 2003, Zimmer, Inc. (11 pages).

"MOST Options™ —Limb Salvage Surgery", 2005, Zimmer, Inc., www.zimmer.com (2 pages).

"LCS®/UNI™ Unicompartmental Knee System with Porocoat® Porous Coating", Surgical Technique Booklet, 1998, DePuy Orthopaedics, Inc. (14 pages).

"Zimmer MOST Options ™ System", 2006 Zimmer, Inc., www.zimmer.com (1 page).

Unofficial Machine Translation from the European Patent Office Website for DE 42 19 808 C1, 2 pages.

* cited by examiner

TIBIAL INSERT HAVING A REINFORCED KEEL

CROSS-REFERENCE TO RELATED APPLICATIONS

Cross-reference is made to U.S. patent application Ser. No. 11/171,802 titled TIBIAL INSERT AND ASSOCIATED SURGICAL METHOD, which was filed on Jun. 30, 2005 by James Matthew Rhodes and Jordan Soonja Lee, was assigned to the same assignee as the present application, and is hereby incorporated by reference herein. Cross-reference is further made to U.S. patent application Ser. No. 11/425,936 entitled TIBIAL INSERT AND METHOD FOR IMPLANTING THE SAME by James Matthew Rhodes and Jordan Soonja Lee; U.S. patent application Ser. No. 11/425,921 entitled TIBIAL INSERT HAVING MULTIPLE KEELS by James Matthew Rhodes and Jordan Soonja Lee; and U.S. patent application Ser. No. 11/425,947 entitled TIBIAL INSERT HAVING A KEEL INCLUDING A BORE FORMED THEREIN by James Matthew Rhodes and Jordan Soonja Lee, each of which is assigned to the same assignee as the present application, each of which is filed concurrently herewith, and each of which is hereby incorporated by reference.

FIELD OF THE DISCLOSURE

The present disclosure relates generally to orthopaedic prostheses, and particularly to tibial inserts and the keel portion of the tibial insert.

BACKGROUND

During the lifetime of a patient, it may be necessary to perform a joint replacement procedure on the patient as a result of, for example, disease or trauma. For example, many knee replacement surgeries are performed each year. Total knee replacement or arthroplasty may involve replacement of the mid-shaft portion of the femur, proximal, distal, and/or total femur, and proximal tibia. Unicompartmental knee replacement or arthroplasty involves unicondylar resurfacing. Unicompartmental knee arthroplasty provides an alternative to total knee arthroplasty for rehabilitating knees when only one condyle has been damaged as a result of trauma or disease such as noninflammatory degenerate joint disease or its composite diagnosis of osteoarthritis or post-traumatic arthritis, for example. As such, unicompartmental knee arthroplasty may be indicated for use in patients undergoing surgery for a severely painful and/or disabled joint damaged as a result of osteoarthritis, traumatic arthritis, rheumatoid arthritis, or a failed previous implant when only one condyle of the knee (medial or lateral) is affected. Further, unicompartmental knee replacements may be "multi-piece" replacements wherein a unicompartmental tibial insert is used to replace each of the medial and lateral condyles of the patient. A single, total femoral component or two partial femoral components may be used to cooperate with the two unicompartment inserts.

Unicompartmental knee replacements are intended to provide increased patient mobility and reduce pain by replacing the damaged knee joint articulation in patients where there is evidence of sufficient sound bone to seat and support the components. Age and activity level factor into all reconstructive procedures and the state of the arthritis determines the treatment. With the advancement of minimally invasive techniques that support unicompartmental knee reconstruction, a growing number of patients are offered this alternative for relief from the disabling pain of arthritis and for the potential benefits of a rapid recovery. Many technical challenges persist, however, with respect to providing less invasive unicompartmental knee surgeries.

SUMMARY

According to one aspect of the present disclosure, a tibial insert includes a platform having an upper bearing surface and a plurality of keels extending downwardly from the platform. Illustratively, none of the longitudinal axes of the keels are parallel to an axis running along an inboard surface of the platform. Further, the longitudinal axis of one of keels may be parallel to the longitudinal axis of another of the keels. Alternatively, the longitudinal axis of one of the keels may intersect the longitudinal axis of another of the keels. Further, these intersecting axes may be orthogonal to each other.

Further illustratively, the plurality of keels defines a total keel volume. A medial portion of the total keel volume, which is located on a medial side of the tibial insert, may be different from (i.e., greater than or less than) a lateral portion of the total keel volume, which is located on a lateral side of the tibial insert.

The plurality of keels may include a first keel and a second keel. Additionally, the plurality of keels may further include a third keel.

The longitudinal axis of each of the keels may be parallel to a bottom surface of the platform and each of the plurality of keels may be substantially the same length. Further, the longitudinal axes of the plurality of keels may not be coaligned with each other.

According to yet another aspect of the present disclosure, a surgical method for knee arthroplasty includes determining the quality of the bone of various sections of a patient's resected tibia, selecting a tibial insert having a keel arrangement which corresponds to areas of poor quality of the patient's resected tibia, forming one or more slots in a surgically-prepared surface of the resected tibia which correspond to the keel arrangement of the selected tibial insert, and inserting the keel arrangement of the tibial insert into the one or more slots.

Illustratively, the tibial insert may be selected from a plurality of tibial inserts having different keel arrangements.

Further illustratively, the one or more slots may be formed in the areas of poor bone quality of the patient's resected tibia.

Additionally, the quality of the bone of various sections of the patient's resected tibia may be determined by placing a template onto the surgically-prepared surface of the resected tibia and pressing a probe into portions of the surgically-prepared surface. The surgical method may further include marking the bone through cut-out portions of the template to indicate areas of poor bone quality. Further, the one or more slots may be formed through cut-out portions of the template which have been marked to indicate areas of poor bone quality.

According to still another aspect of the present disclosure, a tibial insert includes a platform including an upper bearing surface and a keel extending downwardly from the platform. The keel is positioned relative to the platform such that the longitudinal axis of the keel is parallel to a bottom surface of the platform and is arranged in a non-parallel relationship relative to an inboard edge of the platform.

According to yet another aspect of the present disclosure, a tibial insert includes a platform having an upper bearing surface and first and second keels extending downwardly from the platform. A longitudinal axis of the first keel is generally parallel with an inboard surface of the platform and a longitudinal axis of the second keel is generally parallel with the longitudinal axis of the first keel. An anterior face of the second keel may be positioned posteriorly from an anterior face of the first keel. A posterior face of the second keel may also be positioned anteriorly from a posterior face of the first keel. The second keel may be positioned laterally from the first keel and the anterior face of the first keel and the anterior face of the second keel may each be angled. Illustratively, the angle of the anterior face of the first and second keels may be approximately 145 degrees from a bottom surface of the platform. A posterior face of each of the first and second keels may be generally vertical. Further illustratively, the first keel may be longer than the second keel and the second keel may be positioned generally within a posterior portion of the tibial insert. A longitudinal axis of the first keel may be parallel to a longitudinal axis of the second keel. The longitudinal axes of each of the first and second keels may be parallel to an inboard surface of the platform.

According to yet another aspect of the present disclosure, a surgical method for knee arthroplasty includes resecting at least a portion of a condyle to create a surgically-prepared, generally horizontal surface, forming a first slot in the surgically-prepared, generally horizontal surface such that the first slot is positioned between and spaced-apart from an anterior surface of the tibia and a posterior surface of the tibia, forming a second slot in the surgically-prepared, generally horizontal surface such that the second slot is positioned between and spaced-apart from the anterior surface of the tibia and the posterior surface of the tibia, and inserting (i) a first keel of a tibial insert into the first slot formed in the surgically-prepared, generally horizontal surface and (ii) a second keel of the tibial insert into the second slot formed in the surgically-prepared, generally horizontal surface.

Illustratively, the first keel may be inserted into the first slot by (i) inserting a posterior end of the first keel into the first slot, (ii) sliding the first keel in a posterior direction such that the posterior end of the first keel engages the posterior end of the first slot, and (iii) pivoting the tibial insert downwardly such that a second end of the first keel is positioned within the first slot. Similarly, the second keel may be inserted into the second slot by (i) inserting a posterior end of the second keel into the second slot, (ii) sliding the second keel in a posterior direction such that the posterior end of the second keel engages the posterior end of the second slot, and (iii) pivoting the tibial insert downwardly such that a second end of the second keel is positioned within the second slot.

Further illustratively, the second slot may be parallel to the first slot and may further include an anterior end that is positioned posteriorly from an anterior end of the first slot. Additionally, forming the second slot may be positioned laterally from the first slot.

According still another aspect of the present disclosure, a tibial insert includes a platform having an upper bearing surface and a keel extending downwardly from the platform. The keel includes a lateral bore formed therein. The lateral bore may be parallel to a lateral axis of the keel or may be positioned to define a non-parallel relationship with the lateral axis of the keel. Further, the lateral bore of the keel may be generally perpendicular to the longitudinal axis of the keel. Illustratively, the keel includes a medial, downwardly-extending surface, a lateral, downwardly-extending surface, and a rounded, distal surface defining a continuous radius connecting the first and second downwardly-extending surfaces and the lateral bore of the tibial insert extends from the medial, downwardly-extending surface of the keel to the lateral, downwardly-extending surface of the keel. Further, the lateral bore may be substantially centrally-located between a bottom surface of the platform and the rounded, distal surface of the keel. The lateral bore may extend entirely through the width of the keel or may extend only partially through the width of the keel. Further, the keel of the tibial insert may include a second lateral bore formed therein.

According to yet another aspect of the present disclosure, a tibial insert assembly includes a tibial insert having (i) a platform including an upper bearing surface and (ii) a keel extending downwardly from the platform and including a lateral bore formed therethrough. The assembly further includes a fastener configured to be received through the lateral bore of the tibial insert after the tibial insert is implanted in a patient's tibia. The tibial insert of the assembly may further include a second lateral bore formed through the keel. As such, the tibial insert assembly may further include a second fastener configured to be received through the second lateral bore after the tibial insert is implanted in a patient's tibia.

According to still another aspect of the present disclosure, a surgical method for knee arthroplasty includes resecting at least a portion of a condyle to create a surgically-prepared, generally horizontal surface, forming a slot in the surgically-prepared, horizontal surface, inserting a keel of a tibial insert into the slot, and inserting a fastener in a medial-lateral direction through keel.

The keel may include a bore through a width of the keel such that the fastener may be inserted through the bore of the keel. Further, a passageway may be drilled from a medial surface of the tibia in a lateral direction through the tibia to intersect the slot formed in the surgically-prepared, generally horizontal surface. The fastener may then be inserted into the passageway and through the lateral bore of the keel. The passageway formed in the tibia may be filled with cement. Drilling the passageway may be performed prior to inserting the keel of the tibial insert into the slot or may be performed after inserting the keel of the tibial insert into the slot.

According to yet another aspect of the present disclosure, a method of manufacturing a tibial insert includes inserting a rod into a lateral bore formed in the tibial insert and applying a surface treatment to an outer surface of the tibial insert when the rod is positioned in the lateral bore. The surface treatment may be applied by (i) engaging the rod with a mechanical handler to avoid touching the tibial insert and (ii) removing the rod from the lateral bore of the tibial insert after applying the surface treatment to the outer surface of the tibial insert. A second rod may also be inserted into a second lateral bore of the tibial insert.

According to still another aspect of the present disclosure, a tibial insert includes a platform having an upper bearing surface, a keel extending downwardly from the platform, and a rod spaced-apart from the platform and positioned to extend through a portion of the keel. Illustratively, the keel and the platform may be made from a first material and the rod may be made from a second material. Further illustratively, the keel and the platform may be made from a polymer and the rod may be made from a metal.

The rod may be positioned along the length of the keel or along the width of the keel or may include a first rod positioned along the length of the keel and a second rod positioned along the width of the keel. The first rod and the second rod may intersect each other. Illustratively, the longitudinal axis of the keel and the longitudinal axis of the rod may be positioned along an anterior-posterior direction.

The keel may include an anterior face and a posterior face such that a first end of the rod is generally planar with the anterior face of the keel and a second end of the rod is positioned within the keel and is spaced-apart from the posterior face of the keel.

The rod may be solid or the rod may be hollow to define an outer shell and an inner passageway. Illustratively, the keel may further include interior passageways in fluid communication with the inner passageway of such a hollow rod. The keel may further include a channel defined in an outer surface of the keel. This channel may be in fluid communication with the interior passageways of the keel. The hollow rod may include apertures formed in the outer shell to provide fluid communication between the inner passageway of the hollow rod and the interior channels of the keel.

According to another aspect of the present disclosure, a tibial insert includes a platform having an upper bearing surface, a keel extending downwardly from the platform, and a rod positioned within at least a portion of the keel such that longitudinal axis of the rod is parallel to the longitudinal axis of the keel. Illustratively, the keel may be longer than the rod or may be generally the same length as the rod.

According to still another aspect of the present disclosure, a surgical method for knee arthroplasty includes resecting at least a portion of a condyle of a patient's tibia to create a surgically-prepared tibial surface, positioning a tibial insert on the surgically-prepared tibial surface, and injecting bone cement into a passageway formed through a rod positioned within the keel of the tibial insert. The bone cement may be injected through the passageway and into a space defined between an outer surface of the keel and a portion of the patient's tibia. Alternatively, the space may be defined by a channel formed in an outer surface of the keel. Additionally, the bone cement may be forced through interior passageways of the keel which fluidly connect the passageway of the rod with the channel of the keel.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
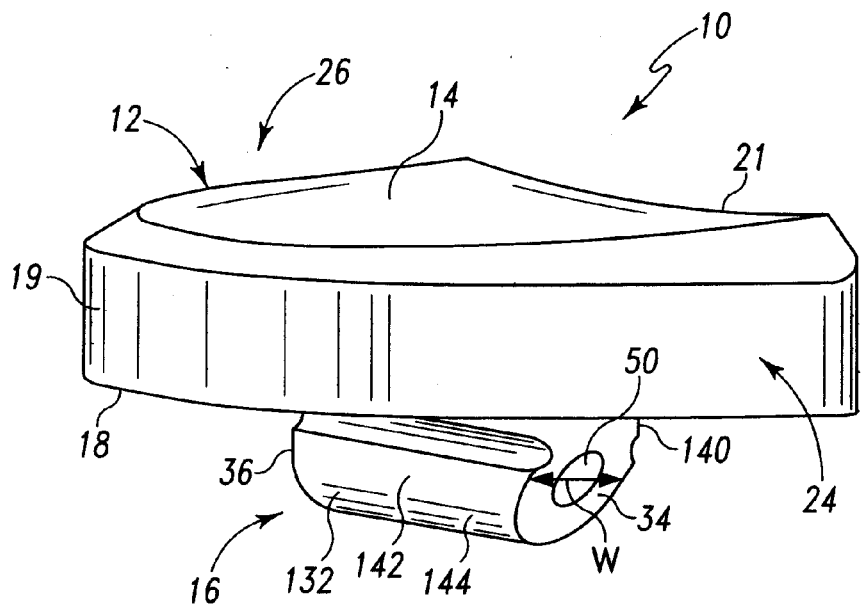
FIG. 1 is a perspective view of a unicompartmental tibial insert showing a keel of the insert and a solid reinforcement rod extending along an anterior-posterior length of the keel.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Figure 2:
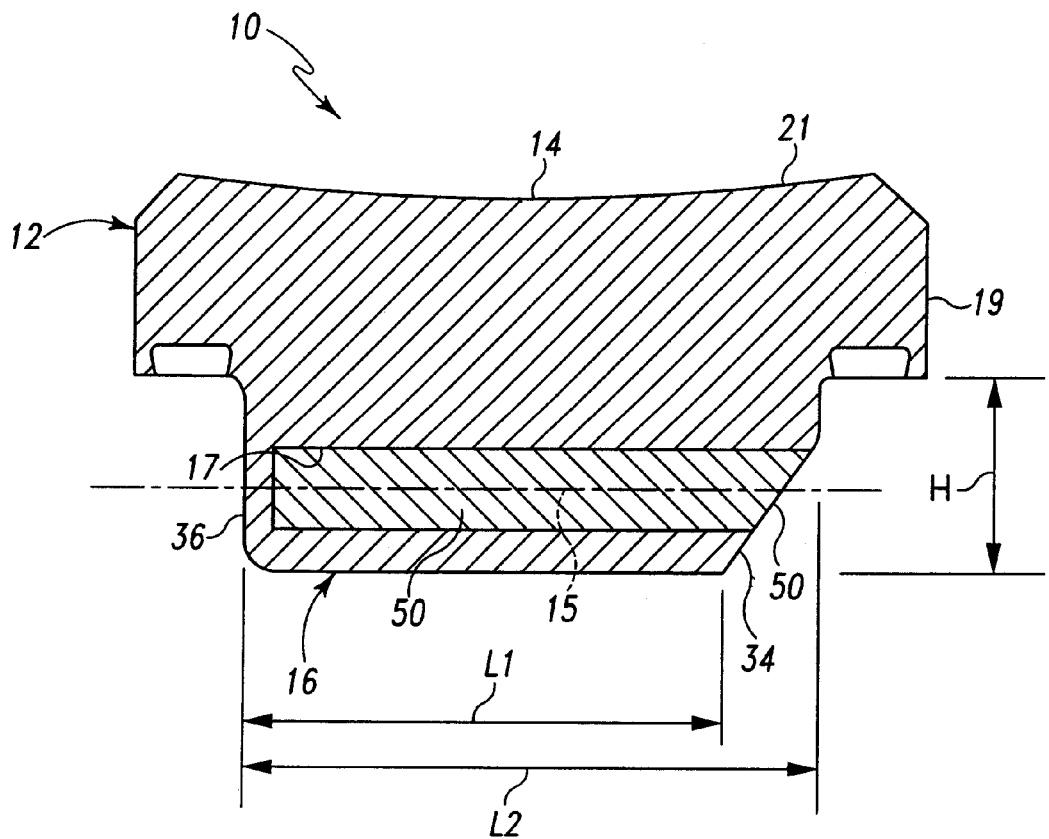
FIG. 2 is a sectional view of the tibial insert of FIG. 1.
Figure 7:
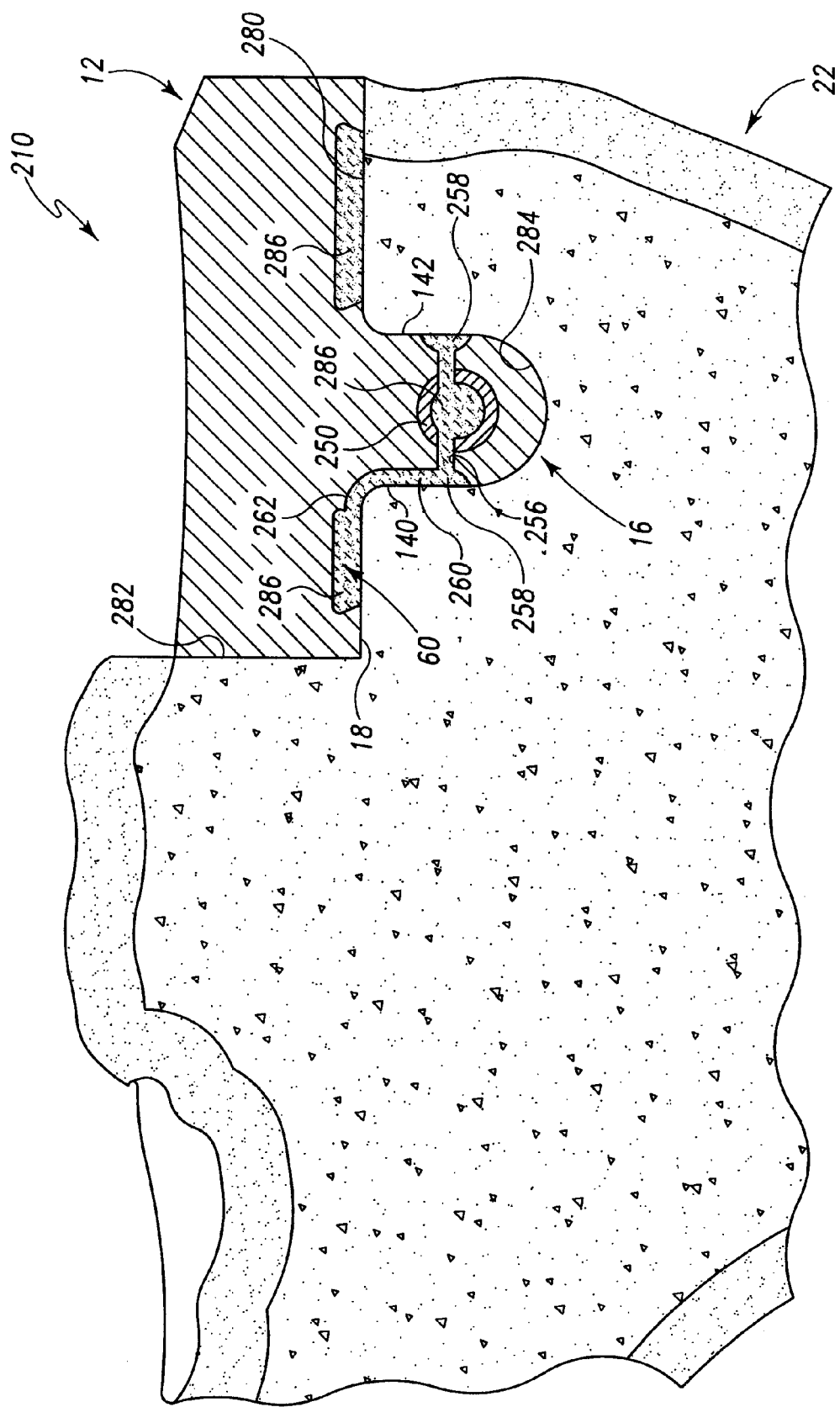
FIG. 7 is a sectional view of the tibial insert of FIGS. 5 and 6 positioned within a slot formed in a patient's tibia and showing bone cement having been injected into the hollow reinforcement rod to fill the passageway of the rod, the internal channels of the keel, and the external groves of the keel.

As shown in FIGS. 1 and 2, a tibial insert 10 includes a platform 12 and a keel 16 extending downwardly from the platform 12. Illustratively, the tibial insert 10 is a unicompartmental tibial insert intended to replace only one of the two bearing surfaces of an illustrative tibia 22, as shown in FIG. 7, for example. As such, the tibial insert 10 may be used by a surgeon or other technician during a unicompartmental knee arthroplasty (UKA). Illustratively, the insert 10 as well as other tibial inserts disclosed herein are suitable for use or implantation by surgeons adopting either conventional or minimally invasive surgical methods of performing UKA. Further, although the tibial insert 10 is a unicompartmental tibial insert, it is within the scope of this disclosure that the various features associated with the tibial insert 10, as well as other tibial inserts discussed, may also be associated with tibial inserts typically used during total knee arthroplasty (TKA) to replace both bearing surfaces of the tibia. Further still, it is within the scope of this disclosure for the various features associated with the many tibial insert embodiments disclosed herein to be associated with other types of orthopaedic implants such as orthopaedic implants associated with hips, shoulders, and elbows, for example.

Looking again to FIGS. 1 and 2, the platform 12 is generally "D-shaped" when viewed in a plan view and includes an upper bearing surface 14, a lower surface 18, a curved, outer or outboard surface 19, and a generally straight inner or inboard surface 21. The keel 16 extends from the bottom surface 18 of the platform 12. As is defined herein, the term "keel" means a structure extending downwardly from the bottom surface of the platform for insertion into a portion of a patient's bone during an orthopaedic joint arthroplasty procedure, with such a structure (i) having a longitudinal axis that is arranged generally parallel to a plane defined by the bottom surface of the platform, (ii) lacking radial symmetry along its longitudinal axis, and (iii) has a ratio between a first length, L1, measured along the distal-most edge of the structure and a second length, L2, measured along the edge of the structure which is formed with or abuts the bottom surface of the platform of between 0.15-1.0.

Hence, a keel is distinct from a peg which generally includes a longitudinal axis perpendicular to the plane defined by the bottom surface of the platform of the tibial insert. Further, a peg is oftentimes radially symmetrical along its longitudinal axis. Moreover, a keel is distinct from a fin which typically extends downwardly from the platform to a tip or point thus defining a first length measured along the distal-most edge of the fin which is less than 15% the length of the edge of the fin which abuts the bottom surface of the platform. As such, a keel as used herein is distinct from both pegs and fins of tibial inserts.

As described above, a ratio between the length, L1, measured along the distal-most edge of the keel 16 and the length, L2, measured along the edge of the keel 16 which is formed with or abuts the bottom surface of the platform is between 0.15-1.0. In other words, the length L1 is between 15%-100% of the length L2. In some embodiments, the length L1 may be between 20%-80% of the length L2 while in other embodiments, the length L1 may be between 20%-60% of the length L2. In still other embodiments, the length L1 may be between 20-40% of the length L2.

Figure 4:
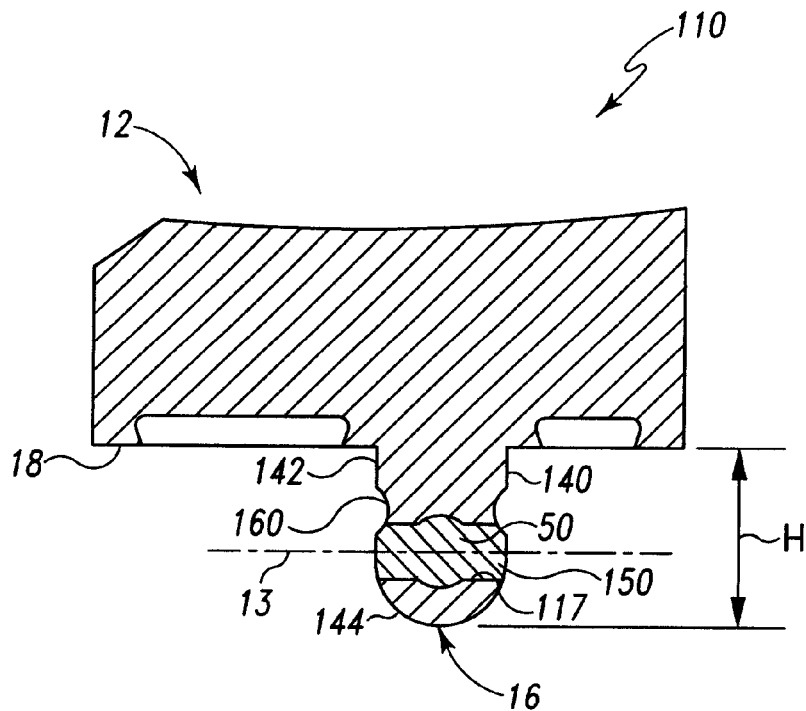
FIG. 4 is a sectional view taken through the second reinforcement rod of the tibial insert of FIG. 3.

Illustratively, the longitudinal axis 15 of the keel 16 of the tibial insert 10 extends in an anterior-posterior direction between an anterior (or front) side 24 of the tibial insert 10 and a posterior (or back) side 26 of the tibial insert. Further, the lateral axis 13 of the keel 16 extends in a medial-lateral direction, as shown in FIG. 4. The keel 16 is dimensioned such that its anterior-posterior length (L1 and/or L2) is greater than its height H. Illustratively, the height H of the keel 16 is measured from the bottom surface 18 of the platform 12 to the distal-most edge of the keel 16 as shown in FIGS. 2 and 4. In other words, the height H of the keel is the distance which the keel extends downwardly from the bottom surface 18 of the platform 12 in the inferior-superior direction. The keel 16 is also longer than it is wide. In particular, the length (L1 and/or L2) of the keel 16 is greater than the width W of the keel 16.

Illustratively, the cross-section of the keel 16 is generally "U-shaped", and, as such, has an outer, curved wall 132. Specifically, the keel 16 includes a rounded distal end which defines a generally semi-circular shape in cross-section. In other words, a portion of the keel 16, and specifically the distal end of the keel 16, forms or defines a 180° arc. As such, the keel includes a generally downwardly-extending medial surface 140, a generally downwardly-extending lateral surface 142, and a rounded, distal surface 144 defining a continuous radius connecting the first and second downwardly-extending surfaces 140, 142. Of course, it is within the scope of this disclosure to include keels having other cross-sectional shapes or squared-off edges, for example.

The keel 16 further includes a passageway 17 extending along the longitudinal axis 15 of the keel 16. Illustratively, the passageway 17 is circular in cross-section; however, it is within the scope of this disclosure to include a passageway having any other suitable cross-sectional shape such as square-shaped, rectangular, and triangular, octagonal, etc. As shown in FIG. 2, the passageway 17 is a blind hole formed in the anterior face 34 of the keel 16. That is, the passageway 17 extends partially through the length of the keel 16 from the anterior face 34 of the keel 16 and terminates within the keel 16 at a point anterior to the posterior face 36 of the keel 16. However, it is within the scope of this disclosure to include a passageway 17 which extends the entire length of the keel 16 (i.e., is open to both the anterior face 34 and the posterior face 36 of the keel 16). Alternatively, the passageway 17 may begin at the posterior face 36 of the keel 16 and terminate at some point within the keel 16 before reaching the anterior face 34 of the keel 16. In another alternative embodiment, the passageway 17 may be located entirely within the interior of the keel 16 without opening to either the anterior face 34 of the keel 16 or to the posterior face 36 of the keel 16.

A solid reinforcement rod 50 is positioned within the passageway 17 of the keel 16. The illustrative reinforcement rod 50 is circular in cross-section and is substantially the same length of the passageway 17. Of course, if the cross-section of the passageway 17 is something other than circular, the cross-section of the reinforcement rod 50 may be likewise shaped. In other words, the reinforcement rod 50 may have a square, rectangular, oval, triangular, octagonal, or other such cross-sectional shape as well.

During manufacture of the tibial insert 10, the passageway 17 may be molded or preformed in of the keel 16. Alternatively, the tibial insert 10 may be molded with a solid keel, the passageway 17 being subsequently drilled or otherwise machined into the keel 16. In either case, once the passageway 17 has been formed to into the keel 16, the reinforcement rod 50 may then be press-fit into the passageway 17. If desired, a cement or glue may be used to secure the reinforcement rod 50 within the passageway 17 of the keel 16. Alternatively, the polymer portions of the tibial insert 10, such as the platform 12 and the keel 16, may be insert molded around the reinforcement rod 50.

Illustratively, the reinforcement rod 50 is solid and is made from a metal or metal alloy such as titanium, stainless steel, or cobalt chromium, for example. Of course, it is within the scope of this disclosure for the reinforcement rod 50 to be made from other suitable metals as well. Further, it is within the scope of this disclosure for the reinforcement rod 50 to be made from one or more materials other than metals such as polymers, ceramics, cements, glass, etc.

As noted above, the platform 12 and keel 16 are illustratively made from a polymer such as UHMWPE (ultra high molecular weight polyethylene) for example. However, the keel 16 and the platform 12 may be made from other materials suitable for implantation into the human body. The reinforcement rod 50 is harder and/or more rigid than the polymer material from which the keel 16 is made. As such, the reinforcement rod 50 increases the stiffness or rigidity of the keel 16 while still allowing the keel 16 to possess an outer shell made from a polymer material.

Figure 3:
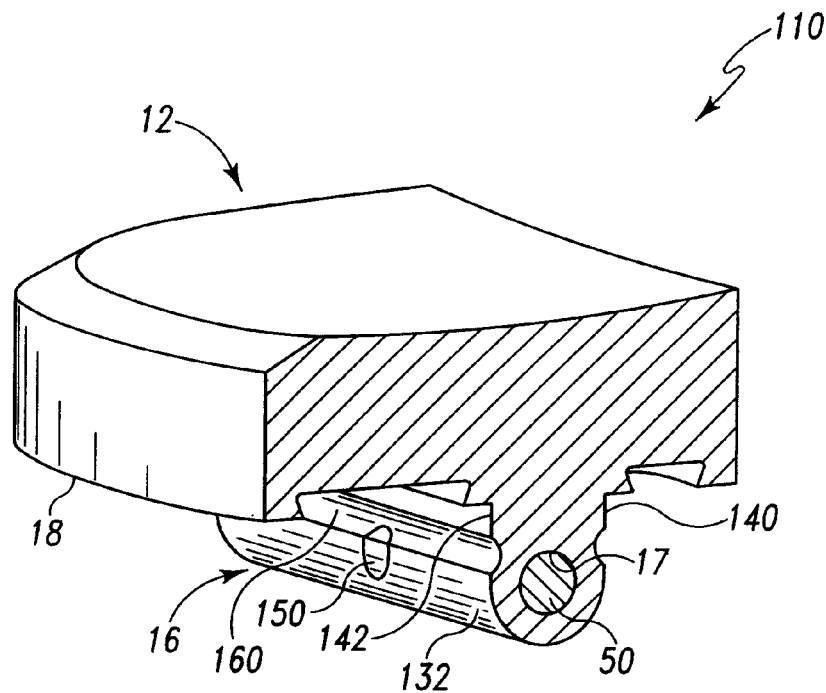
FIG. 3 is a sectional view of another unicompartmental tibial insert showing a first solid reinforcement rod extending along the anterior-posterior length of the keel and a second solid reinforcement rod extending along a medial-lateral width of the keel.

Looking now to FIGS. 3 and 4, there is shown a tibial insert 110 that is somewhat similar to the tibial insert 10. Like reference numerals have been used in FIGS. 3 and 4 to designate features which are similar to those designated in FIGS. 1 and 2. A second solid rod 150 of the tibial insert 110 is positioned within a second passageway 117 of the keel 16 and extends in the lateral direction of the keel 16 from the medial surface 140 of the keel 16 to the lateral surface 142 of the keel 16, as shown in FIG. 3. As such, the second solid rod 150 is parallel to the lateral axis 13 of the keel 16. A groove or outer channel 160 is formed in each of the medial and lateral surfaces 140, 142 and extends along the length of the keel 16.

As noted above, the rod 150 of the tibial insert 110 illustratively extends laterally through the keel 16 from the medial surface 140 to the lateral surface 142, as shown in FIG. 4. Illustratively, the rod 150 is parallel to the lateral axis 13 of the keel 16 and intersects the rod 50. As such, the rods 50, 150 may be embodied as an integral structure. Alternatively, the rod 50 may include a passageway through which the rod 150 extends or the rod 150 may include a passageway through which the rod 50 extends. In either case, the rods 50, 150 intersect each other and are illustratively orthogonal to each other. That is, the rod 50 includes a longitudinal axis (not shown) which co-aligns with, or is parallel to, the longitudinal axis 15 of the keel. The rod 150, includes a longitudinal axis (not shown) which extends the medial-lateral direction and is parallel to the lateral axis 13 of the keel 16. As such, the longitudinal axis of the rod 50 and the longitudinal axis of the rod 150 are orthogonal to each other. It is within the scope of this disclosure, however, for the rod 150 to extend from the medial surface 140 of the keel 16 to the lateral surface 142 of the keel 16 at an angle or non-parallel relationship to the lateral axis 13 of the keel 16. Similarly, the rod 50 may also extend in a non-parallel relationship to the longitudinal axis 15 of the keel 16.

Although the passageway 117 and the rod 150 of the tibial insert 110 are each shown to extend from the medial surface 140 of the keel 16 to the lateral surface 142 of the keel 16, it is within the scope of this disclosure to provide a second rod which extends only to either the medial surface 140 of the keel 16 or to the lateral surface 142 of the keel 16. In other words, the passageway 117 may form a blind hole in either the medial or lateral surfaces 140, 142 of the keel 16. Further, the rod 150 may be located entirely internally within the keel 16 such that neither end of the second rod extends to or through either of the medial or lateral surfaces 140, 142 of the keel 16.

It is also within the scope of this disclosure to position the rod 150 at any point along the anterior-posterior length of the keel 16. As shown in FIG. 4, for example, the rod 150 is generally positioned approximately mid-way between the anterior face 34 of the keel 16 and the posterior face 36 of the keel 16. The rod 150, however, may also be positioned further in an anterior direction or in a posterior direction. It is also within the scope of this disclosure to include additional reinforcing rods positioned such that their longitudinal axes are generally parallel to the lateral axis 13 of the keel 16. Such medial-lateral reinforcing rods may be evenly spaced-apart from each other such that a first medial-lateral rod is positioned in an anterior half of the keel 16 while a second medial-lateral rod is positioned in a posterior half of the keel 16, for example. In other embodiments, the medial-lateral rods may be positioned such that each resides within one of the anterior half or posterior half of the keel 16.

Figure 5:
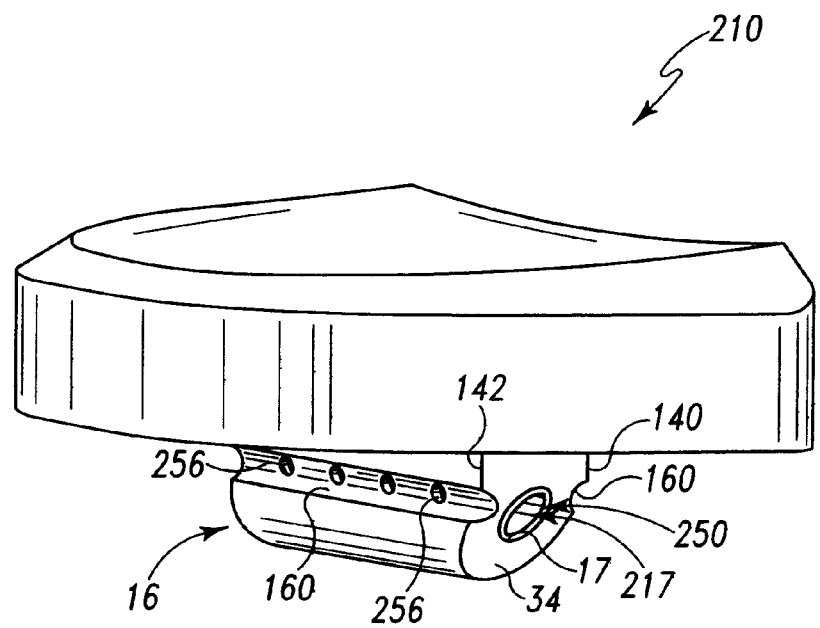
FIG. 5 is a perspective view of yet another unicompartmental tibial insert showing a hollow reinforcement rod extending along the anterior-posterior length of the keel.
Figure 6:
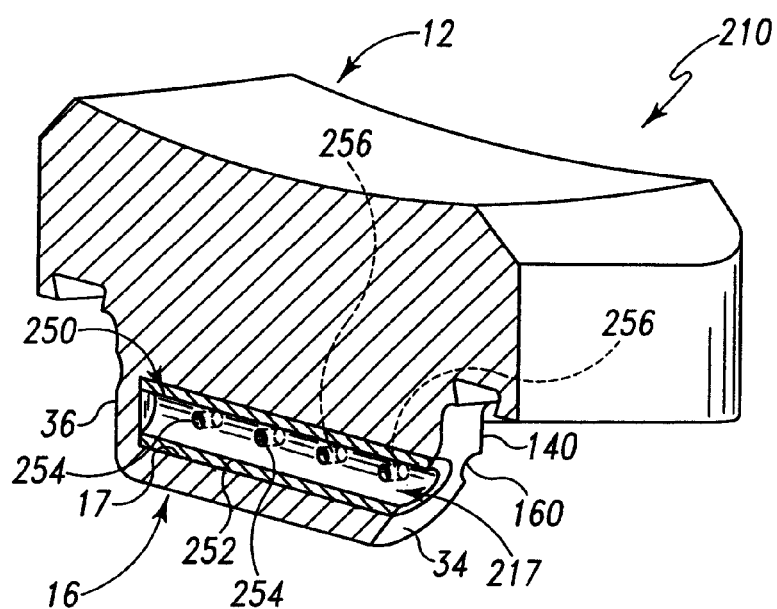
FIG. 6 is a sectional view of the tibial insert of FIG. 5 showing internal channels of the keel in fluid communication with apertures formed in the hollow reinforcement rod.

Looking now to FIGS. 5-7, there is shown another tibial insert 210 that is somewhat similar to the tibial inserts 10, 110 described above. As such, like reference numerals have been used in FIGS. 5-7 to designate features which are similar to those designated in FIGS. 1-4. However, the tibial insert 210 includes an alternative reinforcement rod 250 which is hollow or tubular and defines its own passageway 217 therethrough. As is used herein, the term "rod" refers to both a solid structure such as the solid rods 50, 150 shown in FIGS. 1-4 as well as to a hollow structure such as the hollow rod 250 shown in FIGS. 5-7. In other words, the term "rod" includes both solid and hollow structures.

Looking again to FIGS. 5 and 6, the rod 250 includes an outer shell 252 defining the inner passageway 217. Similar to the solid rods 50, 150 disclosed above, the hollow rod 250 is preferably made from a metal, but may be made from other materials as well. The hollow rod 250 includes an anterior end which is generally planar with the anterior face 34 of the keel 16. However, as shown in FIG. 6, a posterior end of the rod 250 terminates prior to reaching the posterior face 36 of the keel 16. As such, the posterior end of the rod 250 is located internally within the keel 16 and the passageway 17 of the keel 16 is a blind passageway formed in the anterior end of the keel 16, as shown in FIG. 6. It is within the scope of this disclosure, however, for the passageway 17 of the keel 16 as well as the rod 250 of the tibial insert 210 to extend through the length of the keel 16 from the anterior face 34 to the posterior face 36 of the keel 16. Alternatively, the rod 250 may be positioned such that a posterior end of the rod 250 is generally planar with the posterior face 36 of the keel 16 and an anterior end of the rod 250 terminates at some point within the keel 16 before reaching the anterior face 34 of the keel 16.

The outer shell 252 of the hollow rod 250 further includes apertures 254 formed therethrough. The keel 16 of the tibial insert 210 further includes interior passageways 256 (shown in FIGS. 6 and 7) which extend from the anterior-posterior passageway 17 formed through the keel 16 to exterior channels or grooves 160 formed in each of the medial and lateral surfaces 140, 142 of the keel 16. Further illustratively, the outer shell 252 of the hollow rod 250 includes four apertures 254 positioned along the length of a medial side of the rod 250 and four other apertures 254 positioned along the length of a lateral side of the rod 250. As such, the illustrative keel 16 includes four medial passageways 256 which each extend between one of the medial apertures 254 of the rod 250 and the outer channel or groove 160 formed in the medial surface 140 of the keel 16. The keel 16 further includes four lateral passageways 256 which each extend between one of the lateral apertures 254 of the rod 250 and the outer channel or groove 160 formed in the lateral surface 142 of the keel 16. Accordingly, the passageway 217 through the hollow rod 250 is in fluid communication with the interior passageways 256 of the keel 16 via the apertures 254 and the interior passageways 256 of the keel 16 are in fluid communication with at least one of the outer grooves 160 formed in the keel 16.

It is within the scope of this disclosure to include a hollow rod having any number of apertures formed in the outer shell of the rod and for such apertures to be oriented in any configuration. Further, it is within the scope of this disclosure for the keel to include any number of internal passageways in fluid communication with one or more of the apertures of the rod and in fluid communication with one or more of the grooves formed in the medial and lateral surfaces 140, 142 of the keel 16. The keel 16 and platform 12 may also include other passageways, such as illustrative passageways 260, 262 (shown in FIG. 7) which are in fluid communication with the passageway 217 of the rod 250 and with, for example, recessed portion 60 (also shown in FIG. 7) formed in the bottom surface 18 of the tibial insert 210, for example. Such passageways 260, 262 may be used to inject cement 286 into the recessed portion 60 of the insert 210. Illustratively, passageways 260, 262 are formed in the outer surface of the keel 16 and the bottom surface 18 of the platform 12. However, one or more internal passageways as well as other such external passageways may be formed through portions of the tibial insert 210 in order to fluidly connect one or more recessed portions, such as recessed portion 60, with the passageway 217 of the rod 250.

Looking now to FIG. 7, during a total or partial knee arthroplasty, a portion of a condyle of a patient's tibia 22 is resected to create a surgically-prepared, generally horizontal surface 280, a surgically-prepared, generally vertical surface 282, and a slot 284 formed within a portion of the horizontal surface 280. Once the surfaces 280, 282 and slot 284 have been formed, the tibial insert 210 is then positioned on the horizontal surgically-prepared tibial surface 280 and the keel 16 of the tibial insert 210 is positioned within the slot 284. Bone cement 286 is injected in the passageway 217 of the hollow rod 250. As shown in FIGS. 5 and 6, the anterior end of the rod 250 is accessible to the surgeon to allow the surgeon (or other technician) to inject bone cement 286 directly into the passageway 217. As bone cement 286 is urged into the passageway 217 to fill the passageway 217, the bone cement 286 is also urged to exit the passageway 217 via the apertures 254 formed in the outer shell 252 of the rod 250 and to enter the interior passageways 256 of the keel 16. As additional bone cement 286 is urged into the passageway 217, the bone cement 286 exits the interior passageways 256 of the keel 16 to fill the medial and lateral grooves 160 formed in the outer surfaces 140, 142 of the keel 16. Once the bone cement 286 beings to exit the anterior end of the slot 284 via the medial and lateral grooves 160 of the keel 16, the surgeon is made aware that the bone cement 286 has filled the passageway 217, interior channels 256, and the medial and lateral grooves 160, and may refrain from injecting additional bone cement 286 into the passageway 217.

While the internal passageways 256 of the keel 16 fluidly connect the passageway 217 of the hollow rod 250 with external grooves 160 formed in the keel 16, it is within the scope of this disclosure to include a tibial insert having other interior passageways through the keel 16 and/or the platform 12 which connect with other grooves or recesses, such as recessed area 60, formed in the exterior surfaces of the tibial insert 210. As such, the hollow rod 250 provides an opening or means for injecting bone cement 286 into an interior portion of the tibial insert 210. The interior channels 256, therefore, operate as a means for moving bone cement 286 from a single point of entry to various other areas of the tibial insert 210 which may benefit from the addition of bone cement 286. For example, the tibial insert 210 may include various external spaces, recesses, pockets, or grooves formed within the outer surfaces of the platform 12 and/or the keel 16 to and defined between such outer surfaces and a portion of the patient's tibia 22 into which the insert 10 has been implanted. Filling these spaces with bone cement 286 provides an additional attachment point between the tibial insert 210 and portions of the patient's surrounding tibia 22. In addition to providing a means or entry point for injecting bone cement 286 in the tibial insert 210, the hollow rod 250 and bone cement 286 also operate to stiffen or reinforce the keel 16 once the bone cement 286 hardens.

Figure 8:
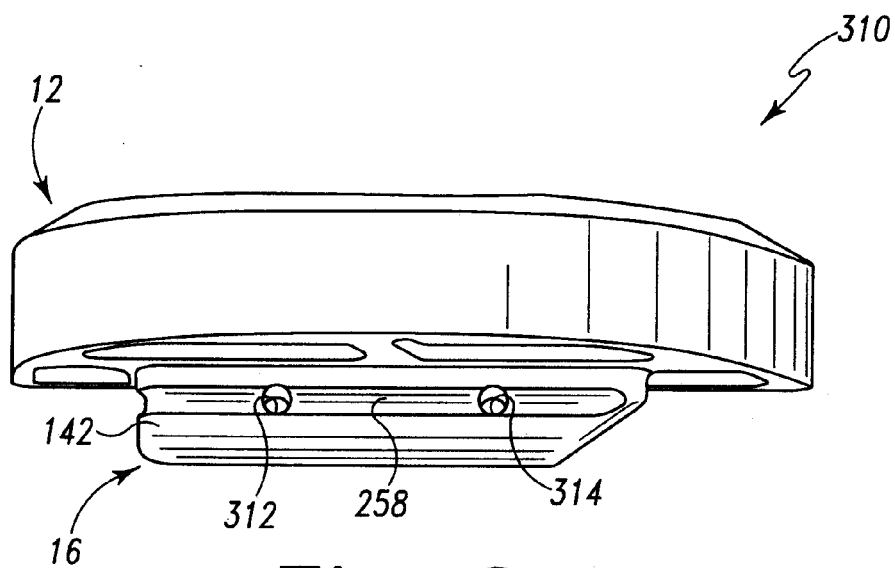
FIG. 8 is a side perspective view of another unicompartmental tibial insert showing a keel of the insert including first and second medial-lateral bores formed through a medial-lateral width of the keel.
Figure 9:
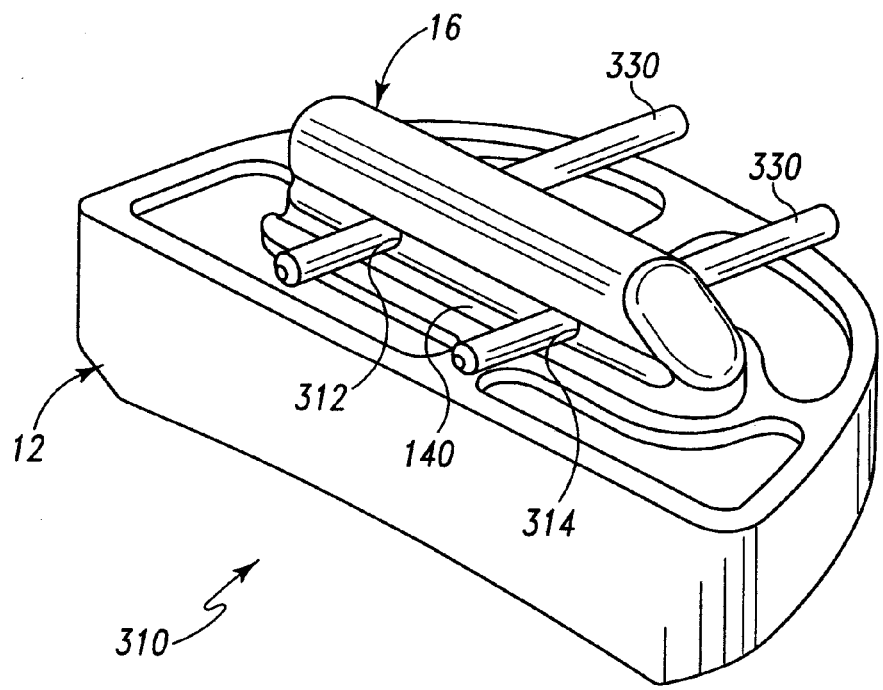
FIG. 9 is a bottom perspective view of the tibial insert of FIG. 8 showing first and second rods received through the first and second bores.
Figure 10:
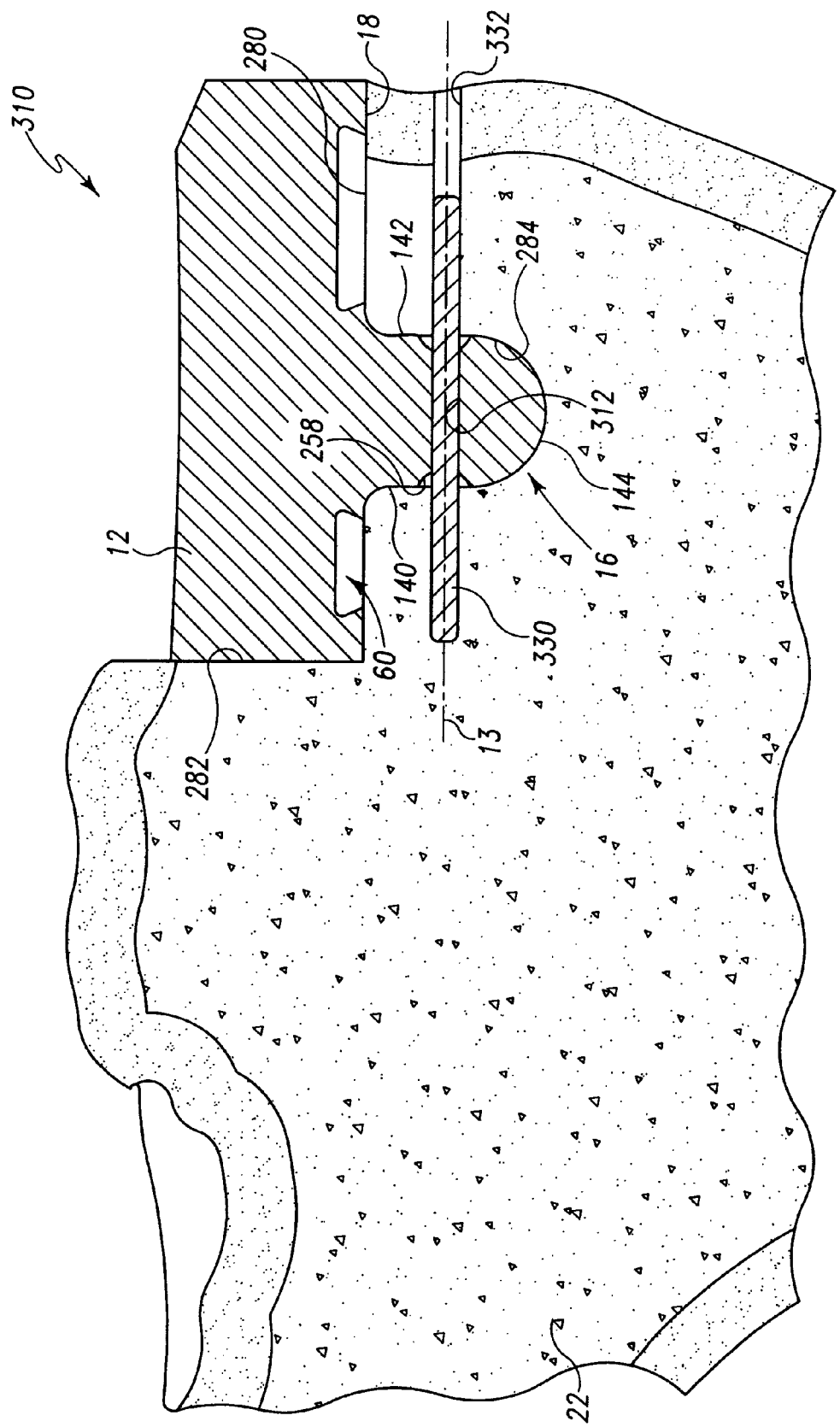
FIG. 10 is a sectional view of the tibial insert of FIG. 8 positioned within a slot formed in a patient's tibia showing the first rod having been inserted into the patient's tibia and through the first medial-lateral bore of the keel to secure the tibial insert to the patient's tibia.

Looking now to FIGS. 8-10, there is shown another tibial insert 310 that is somewhat similar to the tibial inserts 10, 110, 210 described above. As such, like reference numerals have been used in FIGS. 8-10 to designate features which are similar to those designated in FIGS. 1-7. Illustratively, the keel 16 of the tibial insert 310 illustratively includes two lateral bores 312, 314 formed therethrough. That is, the bores 312, 314 each extend laterally across the keel 16 the medial surface 140 to the lateral surface 142 of the keel 16. The bores 312, 314 are spaced-apart from each other along the anterior-posterior length of the keel 16 such that one bore 312 is positioned within a posterior half of the keel 16 while the other bore 314 is positioned within an anterior half of the keel 16.

Illustratively, while two bores 312, 314 are shown, it is within the scope of this disclosure to include a keel 16 having only one bore or to include a keel 16 having more than two bores. Further, any lateral bore or bores of the keel 16 may be positioned at any location along the anterior-posterior length of the keel 16. Further, any lateral bore or bores of the keel 16 may be positioned at any location along the height H of the keel 16. Illustratively, the bores 312, 314, of the keel 16 are shown to be generally centered between the bottom surface 18 of the platform 12 and the distal surface 144 of the keel 16. Further illustratively, an axis (not shown) through each of the bores 312, 314 is generally perpendicular to the longitudinal axis of the keel 16 and is generally parallel to the lateral axis 13 of the keel 16. However, the lateral bores 312, 314 may have a non-parallel relationship with the lateral axis 13 of the keel 16 as well.

Illustratively, as noted above, the bores 312, 314 extend from the medial surface 140 of the keel 16 to the lateral surface 142 of the keel 16. In other words, the bores 312, 314 extend through the width W of the keel 16. It is within the scope of this disclosure, however, for any lateral bore formed in the keel 16 to define a blind bore which extends only partially through the keel 16. In other words, one such blind bore may be formed in the medial surface 140 of the keel 16 whereas another blind bore may be formed in the lateral surface 142 of the keel 16. As such, any lateral bore formed in the keel 16 may extend partially or wholly through the width of the keel 16.

Looking now to FIG. 10, during a total or partial knee arthroplasty, a surgeon may resect at least a portion of a condyle to create the surgically-prepared, generally horizontal surface 280 and the surgically-prepared, generally vertical surface 282, as discussed above with respect to FIG. 7. The surgeon may then form the slot 284 in the surgically-prepared horizontal surface 280 for receiving the keel 16 of the tibial insert 310 therein. Once the slot 284 is formed, the keel 16 of the tibial insert 310 is inserted into the slot 284. A fastener 330 may then be inserted in a medial-lateral direction through one or more of the bores 312, 314 of the keel 16 to further secure the keel 16 of the tibial insert 310 to the surrounding bone 22. The fastener 330 may be a rod (as shown in FIG. 10) or a screw, for example.

Prior to inserting the fastener 330 through the bores 312, 314 of the tibia 22, the surgeon may pre-drill a medial-lateral passageway 332 through the tibia 22. Such passageway 332 may illustratively extend from either the medial or lateral outer surface of the condyle, through the slot 284 formed in the horizontal surface 280 of the condyle and into at least a portion of the patient's bone on the other side of the slot 284 formed in the resected surface. In such a scenario, the passageway 332 may be drilled either before or after the keel 16 of the tibial insert 310 has been positioned within the slot 284. Once the passageway has been formed and the keel 16 of the tibial insert 310 is properly positioned within the slot 284, the surgeon may then insert the fasteners 330 within the pre-drilled passageways to further secure the tibial insert 310 to the patient's tibia 22. The surgeon may also choose to inject bone cement into any pre-drilled passageways prior to positioning the fasteners 330 within the passageways 332. It is, of course, within the scope of this disclosure for the surgeon to simply drill a screw or other fastener into the resected condyle for positioning through the bores 312, 314 of the keel 16 without the need to pre-drill any passageway.

Once the fasteners have been properly positioned through the bores of the keel 16, any portion of the passageway 332 not containing the fastener 330 may be filled with bone cement. Further, in situations where both medial and lateral unicompartmental tibial inserts are implanted into the same tibia, for example, a single fastener, the same as or similar to the fastener 330, may be provided for positioning through a bore of the keel of each separate tibial insert. In other words, a single fastener may be used to secure or anchor two separate unicompartmental inserts to the patient's tibia. Still further, it is within the scope of this disclosure to insert a fastener, such as fastener 330, through the bore of two or more keels of a common tibial insert.

It is also important to note that the bores 312, 314 of the tibial insert 310 may be used during the manufacturing process of the tibial insert 310. Illustratively, the bores 312, 314 may be molded into the tibial insert 310 or may be drilled or machined into or through the keel 16 after the tibial insert 310 has been molded. After the molding process, a surface treatment or surface coating is often applied to the external surfaces of a tibial insert. Such surface coatings include those described in U.S. Pat. No. 6,736,849, for example, the disclosure of which is hereby incorporated by reference herein. Of course, one skilled in the art can appreciate that other types of surface coatings may be applied to the exterior or outer surfaces of the tibial insert as well.

Oftentimes, during the surface coating process, a portion of the tibial insert is masked off in order to be held or grasped by some mechanical handler (not shown) such as a chuck or vice, for example. As such, this masked-off portion of the tibial insert does not receive the surface coating or surface treatment. With the tibial insert 310, however, a rod or rods such as rod 330 may be placed into or through the bore or bores 312, 314 of the keel 16 as shown in FIG. 9. As noted above, the bores 312, 314 may extend entirely or partially through the width of the keel 16 to receive the rod(s) therein. In embodiments where the bores only extend partially through the keel 16, the mechanical handler itself or the rod(s) may be inserted into the partial bore or bores to handle and position the tibial insert without touching or engaging any portion of the outer surfaces of the tibial insert. Such rod(s) may then be grasped by the mechanical handler (or a technician) during the surface coating process such that no portion of the mechanical handler is engaged with the tibial insert. Once the surface coating process is completed, the rods 330 may be removed from the tibial insert 310. Because this process does not require any portion of the tibial insert 310 to be masked-off and/or grasped, all external surfaces of the tibial insert 310 are unimpeded or exposed and available to be treated or coated with the surface coating thus increasing the total surface area of the tibial insert 310 which receives the surface coating.

Looking now to FIGS. 11-14, alternative tibial inserts 410, 510, 610, 710 are provided that are somewhat similar to the tibial inserts 10, 110, 210, 310 described above. As such, like reference numerals have been used in FIGS. 11-14 to designate features which are similar to those designed in FIGS. 1-10. However, the tibial inserts 410, 510, 610, 710 each include a plurality of keels extending downwardly from the platform.

Figure 11:
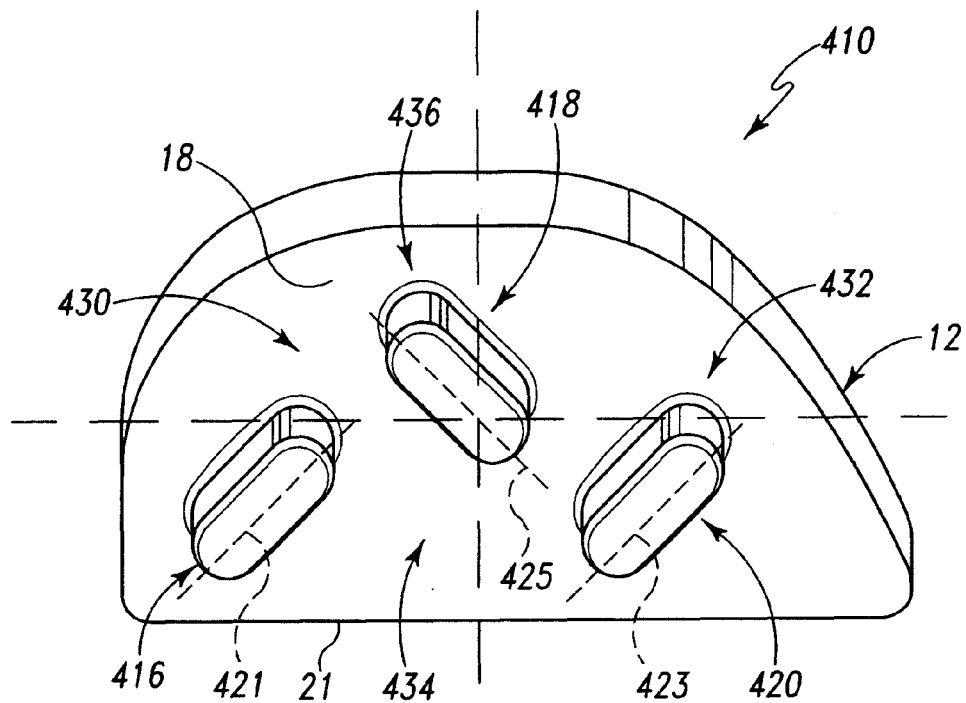
FIG. 11 is a bottom perspective view of another unicompartmental tibial insert having three keels.

Looking first to FIG. 11, for example, the tibial insert 410 includes three keels 416, 418, 420. Illustratively, a longitudinal axis 421 of the keel 416 is parallel to a longitudinal axis 423 of the keel 420 while a longitudinal axis 425 of the keel 418 is generally orthogonal to both the longitudinal axes 421, 423 of the keels 416, 420. Further, none of longitudinal axes 421, 423, 425 of the three keels 416, 418, 420 are parallel to a plane running along the inboard surface or edge 21 of the platform 12. To compare, the longitudinal axis of the keel of the tibial inserts shown in FIGS. 1-10 is generally parallel to a plane running along the inboard surface 21 of the platform 12. Further, the keels 416, 418, 420 of the tibial insert 410 shown in FIG. 11 are not coaligned with each other. In other words, the longitudinal axes of the three keels 416, 418, 420 do not form a single imaginary line running through all three keels 416, 418, 420.

Illustratively, the tibial insert 410, as with any tibial insert disclosed herein, may be divided into sections to generally define an anterior half or side 430 of the tibial insert 410 and a posterior half or side 432 of the tibial insert 410. The tibial insert 410 may also be divided into sections to generally define a medial half or side 434 of the tibial insert 410 and a lateral half or side 436 of the tibial insert 410. As such, the keels disclosed in FIGS. 1-10 are generally positioned such that a substantially equal portion or volume of the keel is positioned on the medial half and the lateral half of the tibial insert. Further, a substantially equal portion or volume of the keels disclosed in FIGS. 1-10 is positioned on the anterior half and the posterior half of the tibial insert.

Looking now to FIG. 11, however, the keels 416 and 420 are generally positioned within the medial half 434 of the tibial insert 410 whereas the keel 418 is generally positioned within the lateral half 436 of the tibial insert. Further, the keel 416 is generally positioned within the anterior half 430 of the tibial insert 410 while the keel 420 is generally positioned within the posterior half 432 of the tibial insert 410. The volume of each of the three keels 416, 418, 420 may be combined to arrive at a total keel volume of the tibial insert 410. As such, a portion of the total keel volume of the tibial insert 410 which is positioned within the medial half 434 of the tibial insert 410 is greater than a portion of the total keel volume which is positioned within the lateral half 436 of the tibial insert 410.

Figure 12:
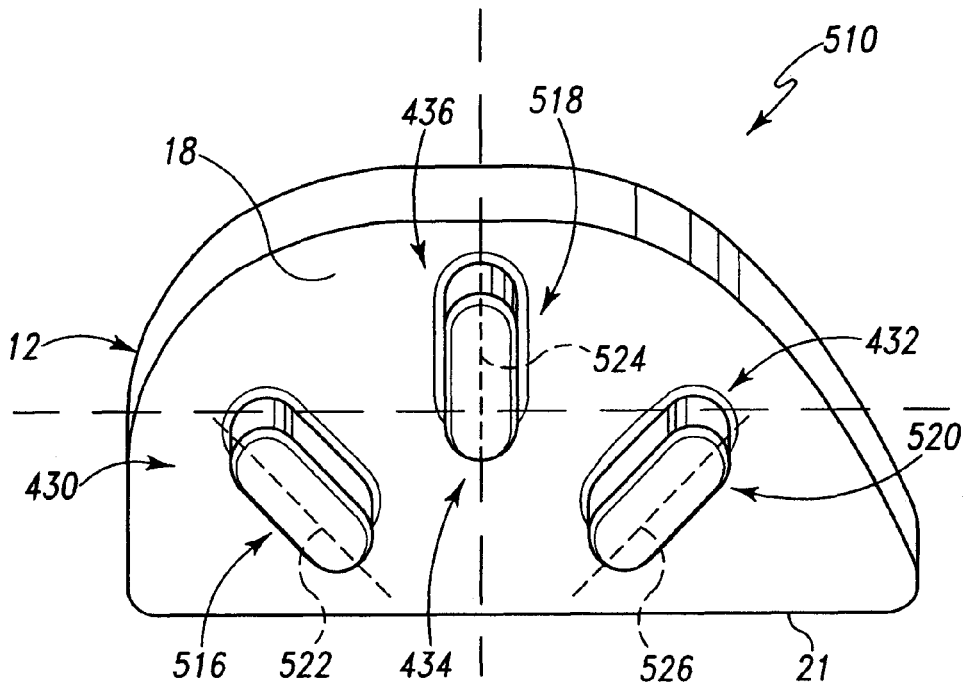
FIG. 12 is a bottom perspective view of another unicompartmental tibial insert having three keels oriented in a manner different than that shown in FIG. 11.

Looking now to FIG. 12, the tibial insert 510 also includes three keels 516, 518, 520 coupled to the platform 12 and extending downwardly from the bottom surface 18 of the platform 12. The keels 516, 518, 520 are arranged such that the longitudinal axes 522, 524, 526 of all three keels 516, 518, 520 intersect each other. Further, the longitudinal axes 522, 526 of the keels 516 and 520 are orthogonal to each other while the longitudinal axis 524 of the keel 518 bisects the longitudinal axes 522, 526 of the keels 516 and 520. Illustratively, the longitudinal axis 524 of the keel 518 is generally orthogonal to a plane running along the inboard edge 21 of the platform 12. Similar to the keels 416, 418, 520 of the tibial insert 410, the longitudinal axes 526, 518, 520 of the keels 516, 518, 520 of the tibial insert 510 are not co-aligned with each other.

In regards to the orientation of the keels 516, 518, 520 of the tibial insert 510, the keel 518 is generally positioned within the lateral half 436 of the tibial insert 510 and is generally centered between the anterior half 430 of the tibial insert 510 and the posterior half 432 of the tibial insert 510. The keel 516 is generally located within the anterior half 430 of the tibial insert 510 while the keel 520 is generally located within the posterior half 432 of the tibial insert 510. Further, a portion of the total keel volume of the tibial insert 510 which is positioned within the medial half 434 of the tibial insert 510 is greater than a portion of the total keel volume which is positioned within the lateral half 436 of the tibial insert 510.

Figure 13:
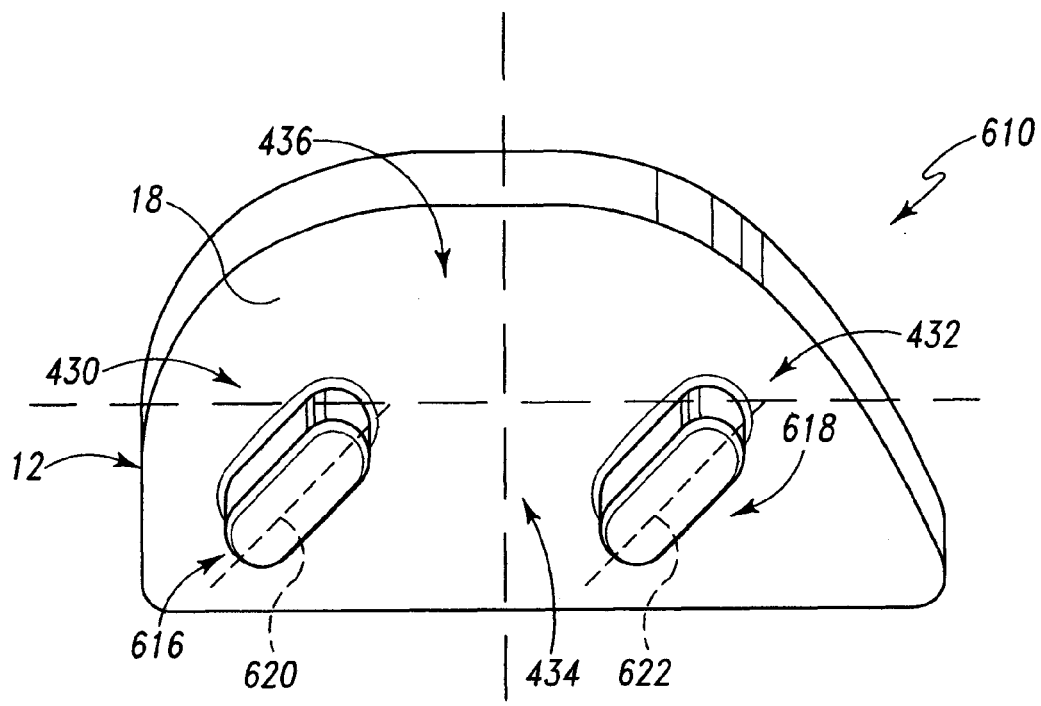
FIG. 13 is a bottom perspective view of another unicompartmental tibial insert having two substantially parallel keels.

Looking now to FIG. 13, the tibial insert 610 includes two keels 616, 618. Illustratively, the longitudinal axes 620, 622 of the keels 616, 618 are parallel to each other. The keels 616, 618 (and thus the corresponding longitudinal axes 620, 622 of the keels 616, 618) are not co-aligned with each other along a common axis. Further, the keel 616 is generally positioned within an anterior half 430 of the tibial insert 610 while the keel 618 is generally positioned within a posterior half 432 of the tibial insert 610. Further, both keels 616, 618 are generally positioned at least mostly within the medial half 434 of the tibial insert 610. As such, a portion of the total keel volume of the tibial insert 610 which is positioned within the medial half 434 of the tibial insert 610 is great than any portion of the total keel volume which is positioned within the lateral half 436 of the tibial insert 610.

Figure 14:
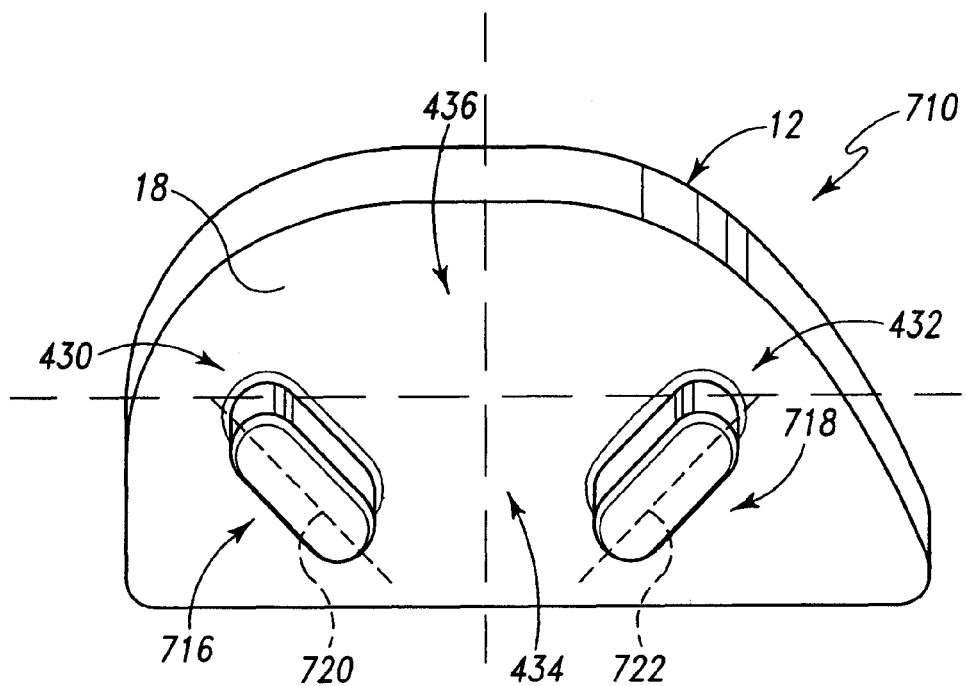
FIG. 14 is a bottom perspective view of another unicompartmental tibial insert having two substantially orthogonal keels.

Looking now to FIG. 14, the tibial insert 710 includes two keels 716, 718. Illustratively, the longitudinal axes 720, 722 of the keels 616, 618 are orthogonal to each other. Further, the keel 716 is generally positioned within an anterior half 430 of the tibial insert 710 while the keel 618 is generally positioned within a posterior half 432 of the tibial insert 710. Further, both keels 716, 718 are generally positioned at least mostly within the medial half 434 of the tibial insert 710. As such, a portion of the total keel volume of the tibial insert 710 which is positioned within the medial half 434 of the tibial insert 710 is greater than any portion of the total keel volume which is positioned within the lateral half 436 of the tibial insert 710. Further, the keels 716, 718 (and thus the longitudinal axes 720, 722 of the keels 716, 718) are not co-aligned with each other along a common longitudinal axis.

The tibial inserts 410, 510, 610, 710 shown in FIGS. 11-14 are meant to be merely illustrative of various tibial inserts having multiple keels and keel arrangements. It is within the scope of this disclosure to include other tibial inserts having any number of keels arranged in any particular manner. In other words, it is within the scope of this disclosure to include tibial inserts having keel arrangements wherein a majority of the total keel volume is located in either the medial half 434 of the tibial insert, the lateral half 436 of the tibial insert, the anterior half 430 of the tibial insert, or the posterior half 432 of the tibial insert. Further, it is within the scope of this disclosure for the keels to be oriented in various positions. For example, one or more keels may have a longitudinal axis that is parallel to the inboard edge 21 of the tibial insert, orthogonal to the inboard edge 21 of the tibial insert, or simply angled or non-parallel to the inboard edge 21 of the tibial insert. It is also within the scope of this disclosure to include keel arrangements having keels of different sizes or dimensions (length, width, and height) than those shown in FIGS. 11-14.

Providing tibial inserts having a wide variety of keel arrangements provides a surgeon with a number of options in choosing which particular tibial insert is most appropriate for the particular patient undergoing TKA or UKA. The term "keel arrangement" refers to the number and orientation of the keels on the tibial insert. In any event, a surgeon performing a TKA or UKA typically begins the procedure by resecting at least one condyle of the patient's tibia. Once the condyle is resected, the surgeon may evaluate and assess the quality of the remaining bone. In particular, resecting the condyle forms a generally horizontal surgically-prepared surface such as surface 280 noted above with regard to FIGS. 7 and 10. The surgeon may evaluate the quality of the patient's bone within this surface. Such an assessment may be fairly subjective to the surgeon. In any event, it is oftentimes preferable to keep or preserve as much "good" quality bone as possible while removing any and all "poor" quality bone. Oftentimes, the "good" quality bone is located where the keel of a typical tibial insert is to be implanted. In such situations, the surgeon is forced to remove this good quality bone to create a slot or bore for receiving the keel of the particular tibial insert to be implanted.

Figure 20:
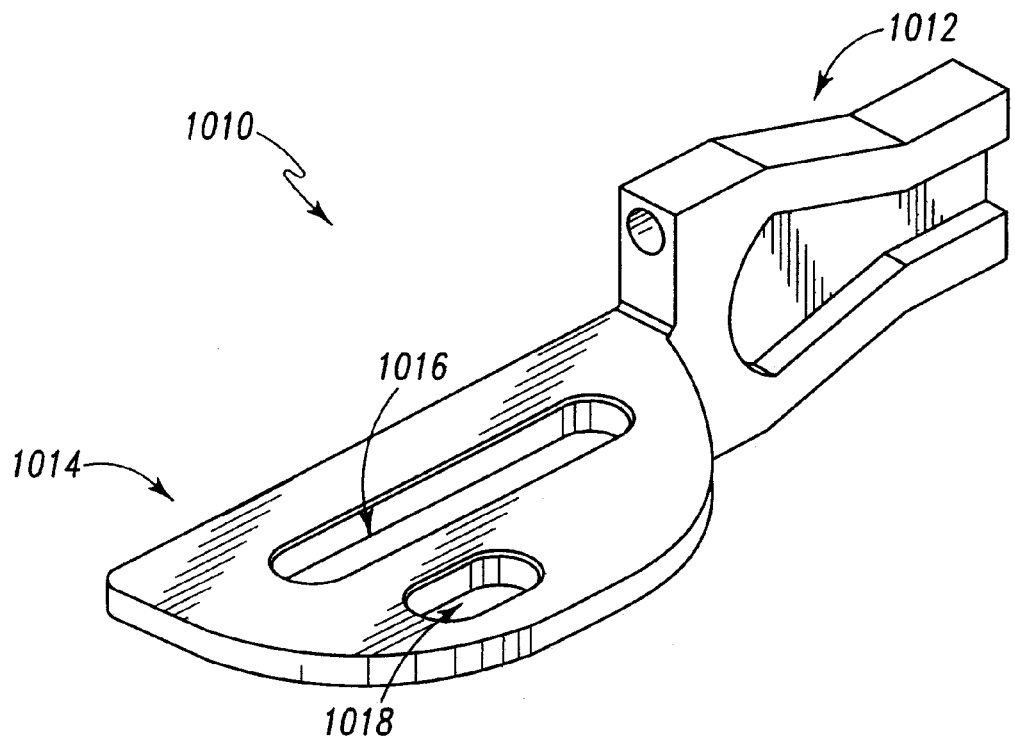
FIG. 20 is a perspective view of a template device which may be used during a knee replacement surgery to aid a surgeon in identifying areas of poor bone quality.

The present disclosure, however, contemplates a variety of tibial inserts available to the surgeon which include a variety of keel arrangements. During surgery, therefore, the surgeon may assess the quality of the patient's bone after the tibia has been resected to create the surgically-prepared, horizontal surface. The surgeon may then note any areas of this surgically-prepared surface of the patient's bone which include "good" or "poor" bone quality. Illustratively, a template, such as the template 1010 shown in FIG. 20 may be used by the surgeon to aide the surgeon in assessing the quality of the exposed bone.

Figure 21:
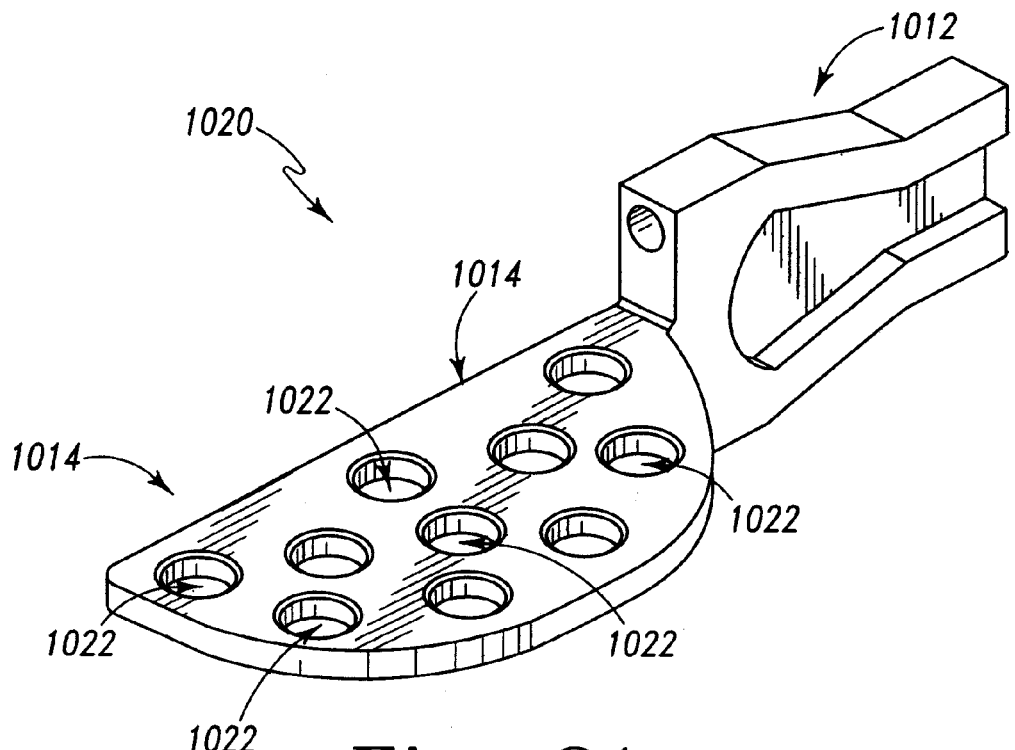
FIG. 21 is a perspective view of another template device.

Looking in particular to FIG. 21, the template 1010 includes a handle 1012 and a platform 1014 coupled to the handle and shaped for use or placement on a surgically-prepared, horizontal surface of a resected tibia. Illustratively, the platform 1014 includes a first slot or cut-out portion 1016 and a second slot or cut-out portion 1018 smaller than and parallel to the first slot 1016. The first slot 1016 and the second slot 1018 correspond to a particular keel arrangement of a tibial insert 810 shown in FIGS. 15-19 (discussed in greater detail below). As such, the template 1010 includes cut-out portions 1016, 1018 which represent a single keel arrangement for a single tibial insert. As such, many various templates may be provided which each include cut-out portions representative of a single keel arrangement of a particular tibial insert. Alternatively, the template 1020 includes an array of cut-out portions 1022 formed through the platform 1014. This array of cut-out portions 1022 may permit the surgeon to assess the quality of various areas of the exposed tibia bone not necessarily associated with the keel arrangement of one particular tibial insert in order to determine which tibial insert from a variety of tibial inserts is best representative of the areas of poor bone quality.

During surgery, for example, the surgeon may place one of the templates 1010, 1020 over the horizontal, surgically-prepared surface of the tibia and may use a probe to check various areas of the horizontal tibial surface to assess the softness or quality of these areas of the bone. For example, when using the template 1010, the surgeon may insert the probe through the cut-out portions 1016 and 1018 to check these areas of the bone and determine whether the tibial insert having a keel arrangement corresponding to these cut-out portions is appropriate. Alternatively, when using the template 1020, the surgeon may probe the bone exposed through the various cut-out portions 1022 to determine which areas of the tibia are of poor bone quality. Illustratively, each cut-out portion 1022 may correspond to a possible anterior end or posterior end of a keel such that once a surgeon determines where areas of poor bone quality exist, a closest corresponding keel arrangement of a particular tibial insert may be determined.

The surgeon may mark on either the patient's bone or on whichever template 1010 or 1020 is used in such a way as to indicate areas of the tibial surface having good and/or poor bone quality. In either case, once the quality of the bone of the horizontal surface has been assessed, the surgeon may then select a tibial insert from the variety of tibial inserts provided which includes a keel arrangement most closely corresponding to the poor bone quality areas of the surgically-prepared surface. Of course, it is within the scope of this disclosure to include various other template devices having any number of cut-out portions which permit a surgeon to probe the surgically-prepared, horizontal surface of the tibia through such cut-out portions in order to determine the quality of the bone.

Once the appropriate tibial insert has been chosen, the surgeon then forms or creates a slot or slots in the surgically-prepared surface which correspond to the keel arrangement of the tibial insert which has been chosen. For example, if the surgeon were to choose the tibial insert 410 shown in FIG. 11, the surgeon would then drill three slots of the same size and orientation as the keels 416, 418, 420 of the tibial insert 410 into the generally horizontal, surgically-prepared surface. The template used by the surgeon may be left in-place on the horizontal surgically-prepared tibial surface to assist the surgeon in determining where to create the slot or slots. Once the appropriate slots are created, the surgeon may then implant the tibial insert by inserting the keels of the tibial insert into the corresponding slots. It is also within the scope of this disclosure to fill each slot with bone cement to further secure the tibial insert to the patient's tibia.

By providing multiple tibial inserts having multiple keel arrangements, a surgeon is better able to customize the tibial insert to the patient. The surgeon is able to choose a tibial insert which allows him to remove areas of poor quality bone while maintaining or preserving as much good quality bone as possible. Further, a tibial insert having multiple keels may operate to increase the rigidity and fixation of the tibial insert within the patient's bone. Further, a tibial insert having multiple keels may also operate to prevent rotational movement of the implanted tibial insert relative to the patient's tibia. As noted above, it is within the scope of this disclosure to include other tibial inserts having other keel arrangements than those disclosed in FIGS. 11-14.

Looking now to FIGS. 15-19, there is shown a tibial insert 810 that is somewhat similar to the tibial inserts described above. As such, like reference numerals have been used in FIGS. 15-19 to designate features which are similar to those designated in FIGS. 1-14. Illustratively, the keel 16 of the tibial insert 810 includes an angled or chamfered anterior surface 834 and a flat or generally vertical posterior surface 836. The angle of the anterior surface 834 is approximately 55 degrees from vertical (or 145 degrees from the bottom surface 18 of the platform 12). However, it is within the scope of this disclosure to include an anterior surface being angled to any suitable degree from vertical. Further still, the anterior surface 834 may be generally vertical, or perpendicular to the bottom surface 18 of the platform 12.

Figure 15:
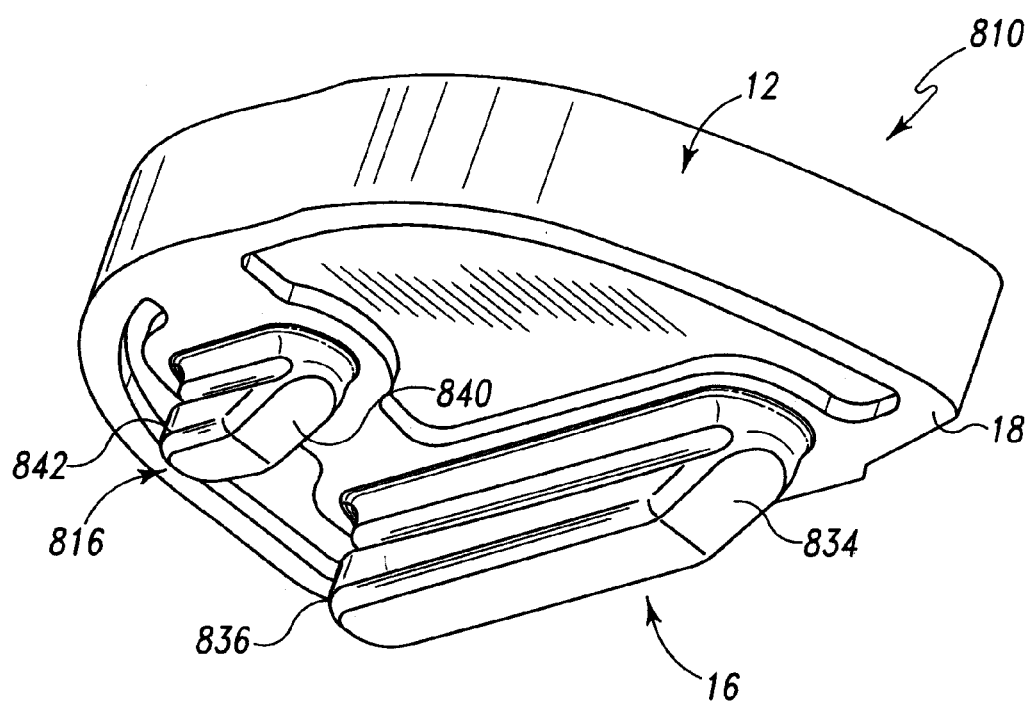
FIG. 15 is a bottom perspective view of another unicompartmental tibial insert having two keels, each keel having an angled anterior face.

The tibial insert 810 further includes a second keel 816 spaced-apart from the first keel 16. As shown in FIG. 15, the second keel 816 is shorter than the first keel 16. Similar to the first keel 16, however, the second keel 816 includes an angled or chamfered anterior surface 840 and a generally vertical posterior surface 842. Illustratively, the angle of the anterior surface 840 of the second keel 816 is approximately 55 degrees from vertical. However, it is within the scope of this disclosure to include an anterior surface being angled to any suitable degree from vertical. Illustratively, the angle of the anterior surface 840 may be between approximately 100-155 degrees from the bottom surface 18 of the platform 12. Further, in some preferred embodiments, the angle may be between approximately 130-145 degrees from the bottom surface of the platform.

Further, illustratively, the anterior surface 840 of the second keel 816 is positioned posteriorly from the anterior surface 834 of the first keel 16. As such, the second keel 816 provides a posterior fixation feature of the tibial insert 810. A posterior fixation feature such as the second keel 816 provides additional posterior support of the tibial insert 810. For example, as a patient's knee is bent, the patient's femur or a femoral component (not shown) moves posteriorly on the bearing surface 14. A posterior fixation feature, such as the second keel 816, provides additional support in such instances to better transmit load from the patient's femur to the patient's tibia. The angled anterior surface 840 of the second (or posterior) keel 816 allows the keel to be positioned further posteriorly than a same or similar keel having a generally vertical anterior surface. Illustratively, therefore, increasing the angle of the anterior surface 840 of the second keel 816 allows the second keel 816 to continue to be positioned further posteriorly relative to the platform 12 from which the keel 16 extends. Further, reducing the height of the second keel 816 also allows the second keel 816 to be positioned further posteriorly on the platform 12 while maintaining the minimally invasive approach for implanting such an insert 810.

As noted above, a minimally invasive approach for implanting such tibial inserts provides for an angled-entry approach due to the minimal clearance provided between the patient's femur and the patient's tibia. As such, the angled anterior surface 840 of the second, posterior keel 816 (as well as the angled anterior surface 834 of the first keel 16) allows the tibial insert 810 to be inserted at an angle and then generally pivoted into place. The angled anterior surfaces 834 and 840 provide sufficient clearance from the anterior ends 860, 882 of the respective first and second slots 850, 880 to make the angled-entry feasible.

Figure 16:
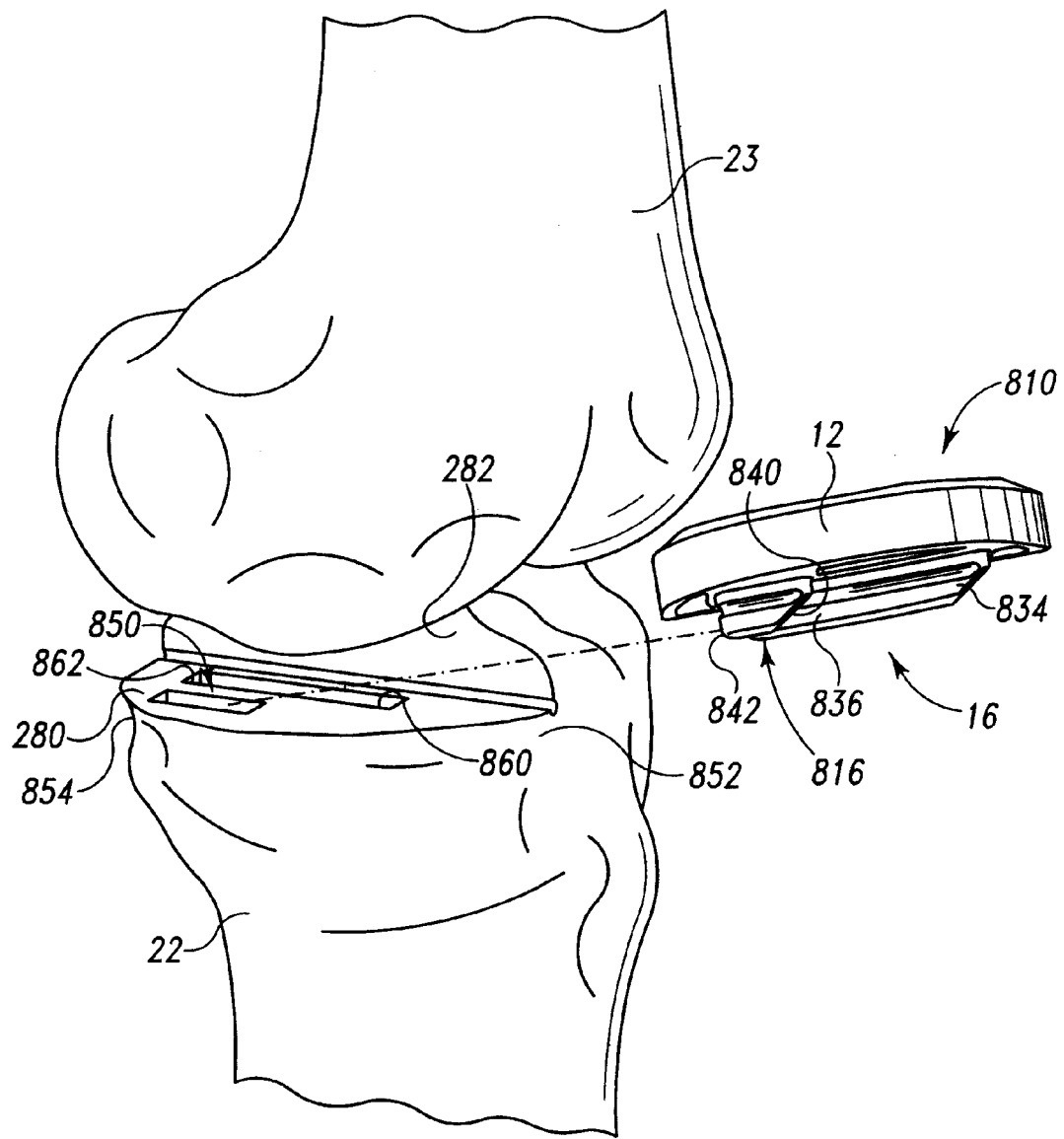
FIGS. 16-18 are side perspective views of the tibial insert of FIG. 15 being inserted into two slots formed in the patient's tibia.

Looking now to FIG. 16, a patient's tibia 22 has been resected to create the surgically-prepared, horizontal surface 280 and the surgically-prepared, vertical surface 282. These surgically-prepared surfaces 280, 282 may be prepared using standard surgical techniques. Further, such surfaces 280, 282 may also be prepared by those techniques disclosed and discussed in U.S. patent application Ser. No. 11/171,802 filed on Jun. 30, 2005.

In any event, once the tibia has been resected, a first slot 850 is formed in the surgically-prepared, horizontal surface 280. The first slot 850 is sized and positioned to receive the first keel 16 of the tibial insert 810 therein. As shown in FIG. 16, the first slot 850 is generally centrally located in an anterior-posterior direction and does not extend to either the anterior surface 852 of the resected tibia 22 or the posterior surface 854 of the resected tibia 22. In other words, an anterior end 860 of the first slot 850 is spaced-apart from the anterior surface 852 of the patient's tibia 22. Similarly, a posterior end 862 of the slot first 850 is spaced-apart from the posterior surface 854 of the patient's tibia 22.

A second slot 880 is also formed in the surgically-prepared, horizontal surface 280. The second slot 880 is sized and positioned to receive the second keel 816 of the tibial insert 810 therein. As shown in FIG. 16, the second slot 880 is spaced-apart in a lateral direction from the first slot 850 and similarly does not extend to either the anterior surface 852 of the resected tibia 22 or the posterior surface 854 of the resected tibia 22. Further, an anterior end 882 of the second slot 880 positioned posteriorly from the anterior end 860 of the first slot 850. Similar to the first slot 850, both the anterior end 882 and a posterior end 884 of the second slot 880 are spaced-apart from the anterior and posterior surfaces 852,854 of the patient's tibia 22.

The first and second slots 850, 880 may be formed by punching or compressing an outline of the shape of the slot into the surgically-prepared horizontal surface 280 of the tibia 22 and then raking away the cut-out portion of the bone. Further, such slots 850, 880 may be formed by 90 degree milling or by using a bone drill at multiple angles and positions. Further, a drill may be used to form an anterior hole and a posterior hole in the surgically-prepared surface 280 of the tibia 22. Once the anterior and posterior holes are formed, the bone between the two holes may be raked away to create the necessary slot. Other method or techniques known to those skilled in the art may also be used to form slots such as the first and second slots 850, 880 described herein.

Figure 17:
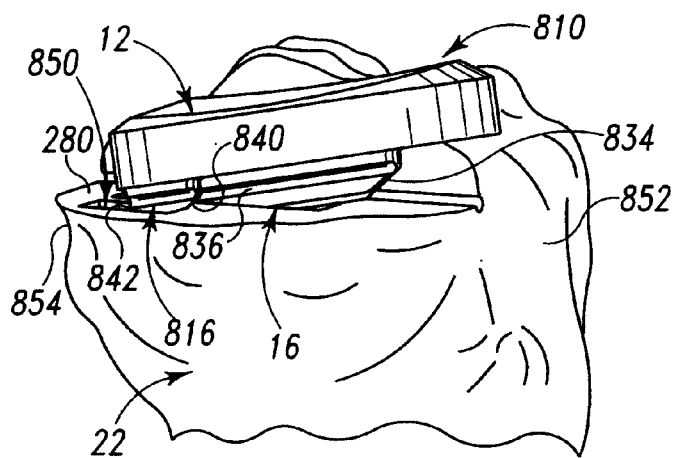

Looking now to FIG. 17, the posterior end 836 of the first keel 16 of the tibial insert 810 is positioned within the first slot 850 formed in the horizontal, surgically-prepared surface 280. Further, the posterior end 842 of the second keel 816 of the tibial insert 810 is positioned within the second slot 880 formed in the tibial surface 280. The surgeon must angle the tibial insert 810 relative to horizontal such that the posterior end of the tibial insert 810 is generally angled downwardly in order to insert the posterior end 836 of the first keel 16 into the first slot 850 and to insert the posterior end 842 of the second keel 816 into the second slot 880.

The degree of angle of this entry may vary depending on the surgeon's particular style or technique and may further depend upon the clearance provided between the tibia 22 and the patient's femur 23. This angled insertion may provide a less invasive means of implanting the tibial insert 810 into the tibia 22 in cases where the slot or slots provided to receive the keel(s) of the tibial insert do not extend to the anterior surface 852 of the tibia 22. Further, sizing the slot(s) formed in the surgically-prepared surface 280 to correspond to the size of the keel(s) to be inserted therein reduces the amount of bone the surgeon must remove from the patient's tibial 22.

Figure 18:
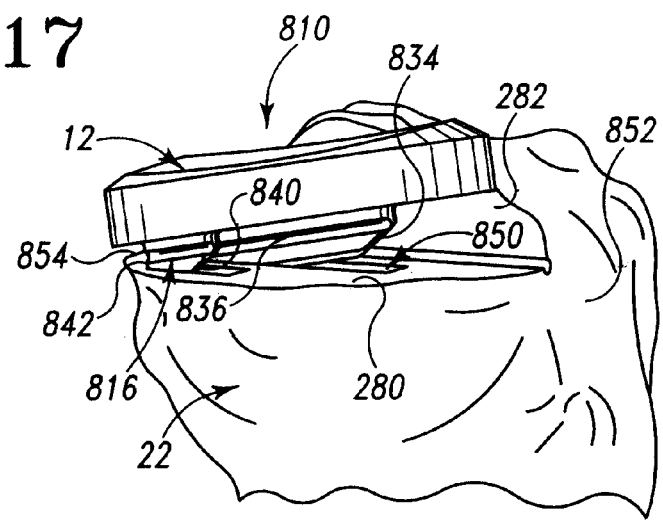
Figure 19:
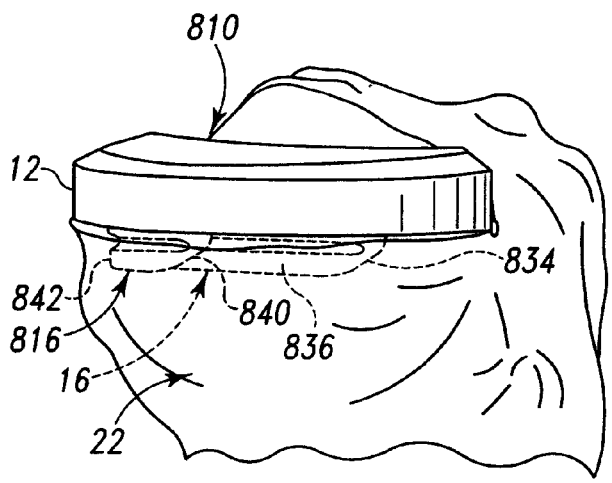
FIG. 19 is a side perspective view of the tibial insert of FIGS. 15-18 fully inserted within the slots formed in the patient's tibia.

The posterior ends 836, 884 of the first and second keels 16, 816 generally remain within the respective first and second slots 850, 880 while the surgeon slides the tibial insert 810 posteriorly. Once the posterior end 836 of the first keel 16 is inserted into the first slot 850 and the posterior end 842 of the second keel 816 is inserted into the second slot 880, the tibial insert 810 is moved or slid posteriorly until the posterior end 836 of the first keel 16 engages the posterior end 862 of the first slot 850 and the posterior end 840 of the second keel 816 engages the posterior end 884 of the second slot 880, as shown in FIG. 18. Once the posterior ends 836, 884 of the first and second keels 16, 816 have engaged the respective posterior ends 862, 884 of the first and second slots 850, 880, the surgeon pushes the anterior end of the tibial insert 810 downwardly or in an inferior direction until the keels 16, 816 are completely received within their respective slots 850, 880, as shown in FIG. 19.

The angled anterior surfaces 834, 840 of the first and second keels 16, 816 provide clearance for the anterior portion of the keels 16, 816 as the tibial insert 810 is generally pivoted downwardly into place within the slots 850, 880. In other words, the angled anterior ends 834, 840 of the first and second keels 16, 816 allows the surgeon to insert the tibial insert 810 at an angle (to reduce the amount of clearance necessary between the patient's tibia and femur) and then pivot the tibial insert 810 downwardly rather than requiring the surgeon to position the tibial insert directly above the slot such that the keel and the slot are aligned with each other, to then uniformly lower the keel of the tibial insert into the slot. As such, the present technique provides a more minimally-invasive approach which does not require as great a clearance or space between the tibia and the femur. Further, a slot or slots which do not extend to either the anterior or posterior surfaces of the tibia are smaller than slots which do extend to one or both of the anterior or posterior surfaces of the tibia. As such, creating a smaller slot, such as the slots 850, 880 shown in FIGS. 16-19, allows the surgeon to remove less bone from the patient's tibia and, therefore, allows the surgeon to preserve as much of the patient's own bone as possible.

Illustratively, the tibial inserts 10, 110, 210, 310, 410, 510, 610, 710, and 810 disclosed herein may include platforms having a skirt overlay such that portions of the platform may lay over and adjacent the outer surface of the tibia of the patient, for example. Further, the tibial inserts 10, 110, 210, 310, 410, 510, 610, 710, and 810 may include inlay portions coupled to the platform and/or keel of the respective inserts which lay into the surgically-prepared horizontal and/or surgically-prepared vertical surfaces of the tibia.

Further illustratively, the platform and keel portions of the tibial inserts 10, 110, 210, 310, 410, 510, 610, 710, and 810 disclosed herein are made from a polyethylene and may be made from UHMWPE (ultra-high molecular weight polyethylene), for example. However, the tibial inserts 10, 110, 210, 310, 410, 510, 610, 710, and 810 may also be made from other materials suitable for implantation into the human body. As noted above, the rods 50, 150, and 250 of the tibial inserts 10, 110, and 210 are illustratively made from a metal such or metal substrate such as titanium, stainless steel, or cobalt chromium, for example. However, such rods 50, 150, 250 may be made from other suitable metals as well. Further, such rods 50, 150, 250 may be made from one or more materials other than metals such as polymers, ceramics, cements, glass, etc.

Further, although the tibial inserts 10, 110, 210, 310, 410, 510, 610, 710, and 810 of the present disclosure are shown and described as unitary or monolithic components, it is within the scope of this disclosure to include tibial inserts having multiple components. For example, a tibial insert of the present disclosure may include a tray component and a bearing component molded to the tray or separate from the tray for cooperation with the tray. Either the tray component or the bearing component may be made from metal, polyethylene, and/or a combination of metal and polyethylene. Illustratively, therefore, the term tibial insert hereby includes both unitary tibial inserts and tibial inserts having separate tray and bearing components.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A tibial insert comprising:
   a polymer platform including an upper bearing surface configured to contact and articulate with a femoral condyle of a patient's femur,
   a polymer keel extending downwardly from the platform, the polymer keel having a midline defining an anterior side and a posterior side of the polymer keel, the polymer platform and the polymer keel forming a monolithic component,
   a hollow rod spaced-apart from the polymer platform and positioned to extend through a portion of the polymer keel such that a first portion of the hollow rod is positioned in the anterior side of the polymer keel and a second portion of the hollow rod is positioned in the posterior side of the polymer keel,
   wherein the hollow rod defines an outer shell and an inner passageway and is formed from a material (i) different from and (ii) having an increased rigidity relative to a polymer material from which the polymer keel and polymer platform are formed; and wherein the polymer keel further includes interior passageways in fluid communication with the inner passageway of the hollow rod.

2. The tibial insert of claim 1, wherein the hollow rod is made from a metal.

3. The tibial insert of claim 1, wherein the hollow rod is positioned along a length of the polymer keel.

4. The tibial insert of claim 1, wherein a longitudinal axis of the polymer keel and a longitudinal axis of the hollow rod are positioned along an anterior-posterior direction.

5. The tibial insert of claim 1, wherein the polymer keel includes an anterior face and a posterior face such that a first end of the hollow rod is generally planar with the anterior face of the polymer keel and a second end of the hollow rod is positioned within the polymer keel and is generally planar with the posterior face of the keel.

6. The tibial insert of claim 1, wherein the polymer keel further includes a channel defined in an outer surface of the polymer keel, the channel being in fluid communication with the interior passageways of the polymer keel.

7. The tibial insert of claim 1, wherein the hollow rod includes apertures formed in the outer shell to provide fluid communication between the inner passageway of the hollow rod and the interior channels of the polymer keel.

8. A tibial insert comprising:
a polymer platform including an upper bearing surface configured to contact and articulate with a femoral condyle of a patient's femur,
a polymer keel extending downwardly from the polymer platform, the polymer platform and polymer keel forming a monolithic component,
a hollow rod defining an outer shell and an inner passageway and positioned within at least a portion of the polymer keel, wherein a longitudinal axis of the hollow rod is parallel to a longitudinal axis of the keel, the hollow rod being formed from a material (i) different from and (ii) having an increased rigidity relative to a polymer material from which the polymer keel and polymer platform are formed; and
wherein the polymer keel further includes at least one interior passageway in fluid communication with the inner passageway of the hollow rod.

9. The tibial insert of claim 8, wherein a length of the polymer keel is greater than a length of the hollow rod.

10. The tibial insert of claim 8, wherein a length of the polymer keel is generally the same as a length of the hollow rod.

11. A tibial insert comprising:
a polymer platform including an upper bearing surface configured to contact and articulate with a femoral condyle of a patient's femur;
a polymer keel extending downwardly from the polymer platform, the polymer platform and polymer keel forming a monolithic component;
a hollow rod defining an outer shell and an inner passageway and positioned within at least a portion of the polymer keel, wherein a longitudinal axis of the hollow rod is parallel to a longitudinal axis of the keel, the hollow rod being formed from a material (i) different from and (ii) having an increased rigidity relative to a polymer material from which the polymer keel and polymer platform are formed; and
wherein the polymer keel further includes an interior passageway in fluid communication with the inner passageway of the hollow rod, and wherein a first end of the hollow rod is generally planar with an anterior face of the polymer keel and a second end of the hollow rod is generally planar with a posterior face of the keel when the hollow rod is positioned within the portion of the polymer keel.

* * * * *